(12) United States Patent
Zhao et al.

(10) Patent No.: US 8,796,509 B2
(45) Date of Patent: Aug. 5, 2014

(54) PLANTS WITH MODIFIED LIGNIN CONTENT AND METHODS FOR PRODUCTION THEREOF

(75) Inventors: Qiao Zhao, Ardmore, OK (US); Fang Chen, Ardmore, OK (US); Richard A. Dixon, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 133 days.

(21) Appl. No.: 12/834,581

(22) Filed: Jul. 12, 2010

(65) Prior Publication Data

US 2011/0010790 A1 Jan. 13, 2011

Related U.S. Application Data

(60) Provisional application No. 61/225,126, filed on Jul. 13, 2009.

(51) Int. Cl.
| | | |
|---|---|---|
| A01H 5/00 | (2006.01) |
| A01H 5/10 | (2006.01) |
| C07H 21/00 | (2006.01) |
| C07H 21/04 | (2006.01) |
| C12N 15/82 | (2006.01) |
| A01H 1/00 | (2006.01) |
| C12N 15/87 | (2006.01) |

(52) U.S. Cl.
USPC ........... 800/295; 800/284; 800/285; 800/286; 800/298; 435/468; 536/22.1; 536/24.5

(58) Field of Classification Search
None
See application file for complete search history.

(56) References Cited

U.S. PATENT DOCUMENTS

| 2004/0031072 A1* | 2/2004 | La Rosa et al. | 800/278 |
| 2008/0229439 A1* | 9/2008 | La Rosa et al. | 800/260 |
| 2008/0274528 A1 | 11/2008 | Dixon et al. | |
| 2008/0313777 A1 | 12/2008 | Dhugga et al. | |
| 2009/0019605 A1 | 1/2009 | Takagi et al. | |

OTHER PUBLICATIONS

Zhong, R., E.A. Richardson, Z-H. Ye. 2007. Two NAC domain transcription factors, SND1 and NST1, function redundantly in regulation of secondary wall synthesis in fibers of Arabidopsis. Planta. 225:1603-1611.*
Wang, H., Q. Zhao, F. Chen, M. Wang, and R. A. Dixon. 2011. NAC domain function and transcriptional control of a secondary cell wall master switch. Plant J. 68:1104-1114.*
Thomas, C. L., L. Jones, D. C. Baulcombe, and A. J. Maule. 2001. Size constraints for targeting post-transcriptional gene silencing and for RNA-directed methylation in Nicotiana benthamiana using a potato virus X vector. Plant J. 25(4):417-425.*
Olhoft, P.M., L.E. Flagel, C. M. Donovan, and D.A. Somers. 2003. Efficient soybean transformation using hygromycin B selection in the cotyledonary-node method. Planta. 216:723-735.*
Zhao, Z., T. Cai, L. Tagliani, M. Miller, N. Wang, H. Pang, M. Rudert, S. Schroeder, D. Hondred, J. Seltzer, and D. Pierce. 2000. Agrobacterium-mediated sorghum transformation. Plant Mol Biol. 44:789-798.*
Nykiforuk, C. L., J. G. Boothe, E. W. Murray, R. G. Keon, H. J. Goren, N. A. Markley, and M. M. Moloney. 2006. Transgenic expression and recovery of biologically active recombinant human insulin from Arabidopsis thaliana seeds. Plant Biotech. J. 4:77-85.*
Klahre, U., P. Crete, S. A. Leuenberger, V. A. Iglesias, and F. Meins Jr. 2002. High molecular weight RNAs and small interfering RNAs induce systemic posttranscriptional gene silencing in plants. PNAS. 99(18):11981-11986).*
Kay, R., A. Chan, M. Daly, and J. McPherson. 1987. Duplication of CaMV 35S promoter sequences creates a strong enhancer for plant genes. Science. 236(4806):1299-1302.*
Guo, H. H., J. Choe, and L. A. Loeb. 2004. Protein tolerance to random amino acid change. PNAS. 101(25):9205-9210.*
Chen, F., and R. A. Dixon. 2007. Lignin modification improves fermentable sugar yields for biofuel production. Nat. Biotech. 25(7):759-761.*
Gould, J., M. Devey, O. Hasegawa, E.C. Ulian, G. Peterson, and R.H. Smith. 1991. Transformation of Zea mays L. using Agrobacterium tumefaciens and the shoot apex. Plant Physiol. 95:426-434.*
Mitsuda et al., "NAC transcription factors, NST1 and NST3, are key regulators of the formation of secondary walls in woody tissues of arabidopsis," The Plant Cell, 19:270-280, 2007.
Tadege et al., "Insertional mutagenesis: a Swiss army knife for functional genomics of M. truncatula," Trends Plant Sci., 10:229-235, 2005.
Tadege et al., "Large-scale insertional mutagenesis using the Tnt1 retrotransposon in the model legume M. truncatula truncatula," Plant J., 54:335-347, 2008.
Zhong et al., "A battery of transcription factors involved in the regulation of secondary cell wall biosynthesis in arabidopsis," The Plant Cell, 20:2763-2782, 2008.
Zhong et al., "Two NAC domain transcription factors, SND1 and NST1, function redundantly in regulation of secondary wall synthesis in fibers of arabidopsis," Planta, 225:1603-1611, 2007.

* cited by examiner

Primary Examiner — Shubo (Joe) Zhou
Assistant Examiner — Jeffrey Bolland
(74) Attorney, Agent, or Firm — Dentons US LLP

(57) ABSTRACT

The invention provides methods for decreasing lignin content and for increasing the level of fermentable carbohydrates in plants by down-regulation of the NST transcription factor. Nucleic acid constructs for down-regulation of NST are described. Transgenic plants are provided that comprise reduced lignin content. Plants described herein may be used, for example, as improved biofuel feedstock and as highly digestible forage crops. Methods for processing plant tissue and for producing ethanol by utilizing such plants are also provided.

22 Claims, 5 Drawing Sheets

FIG. 1A-B

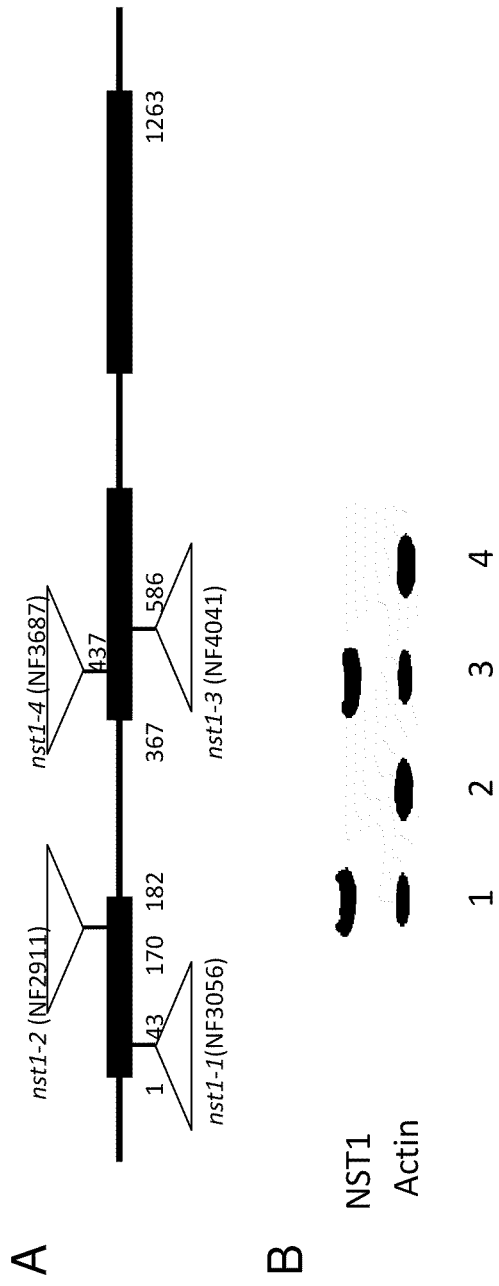
FIG. 2A-B

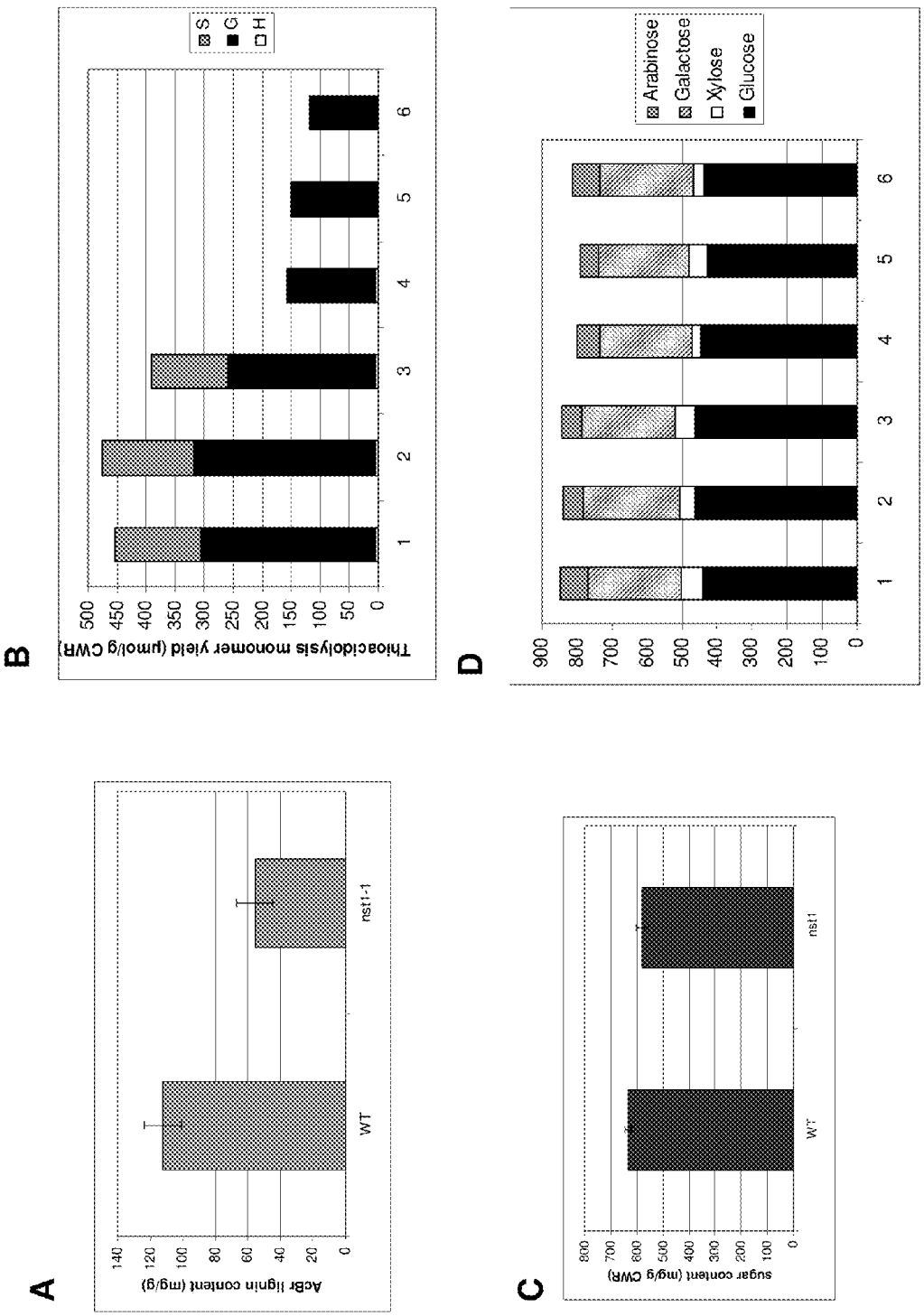
FIG. 3A-D

FIG. 4A-D
A
| Probe sets | Annotation | 1 | 2 | 3 |
|---|---|---|---|---|
| Mtr.33913.1.S1_at | NST1 | 41±0.9 | 131±28 | 477±68 |
| Mtr.40238.1.S1_at | HCT | 3315±187 | 5108±971 | 15782±1155 |
| Mtr.13904.1.S1_at | 4CL | 19±2 | 33±7 | 580±101 |
| Mtr.8589.1.S1_at | CAD | 1437±317 | 2601±498 | 8704±302 |
| Mtr.43183.1.S1_at | C3H | 3603±355 | 5274±579 | 8792±285 |
B
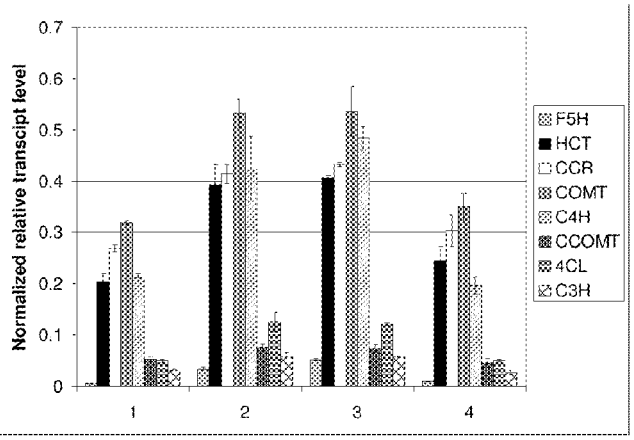
C
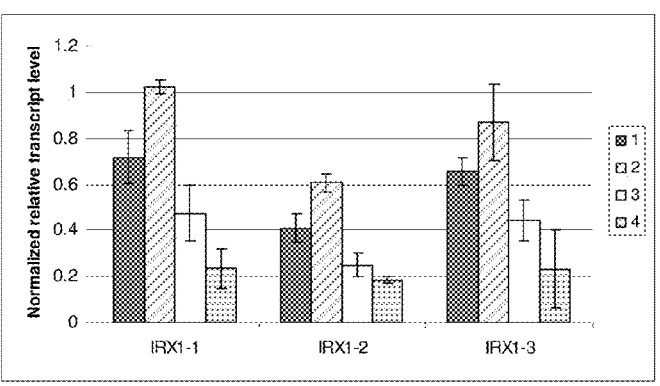
D
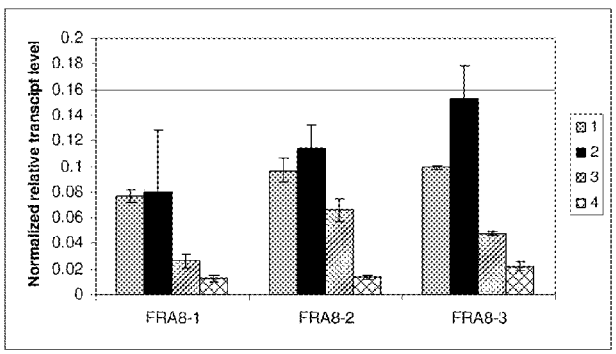

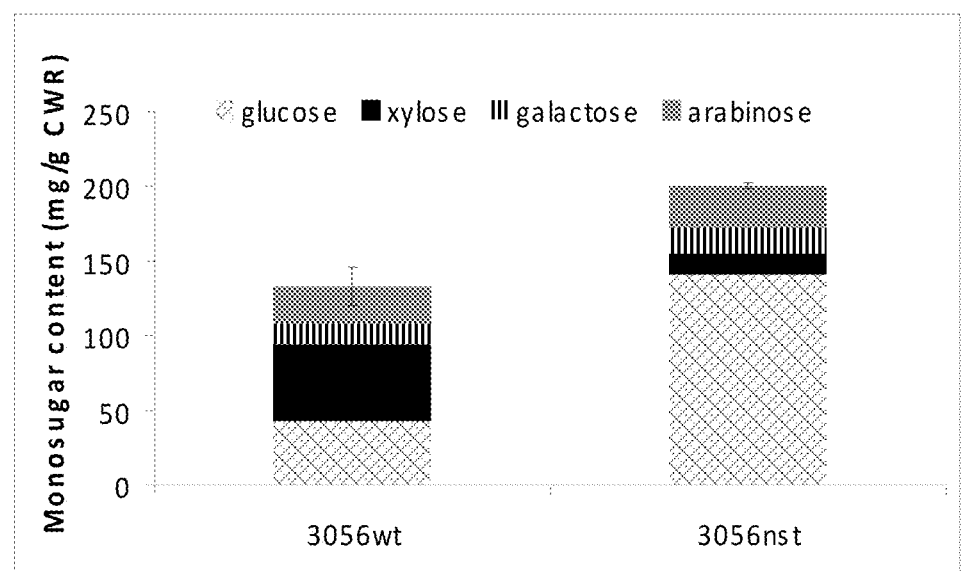
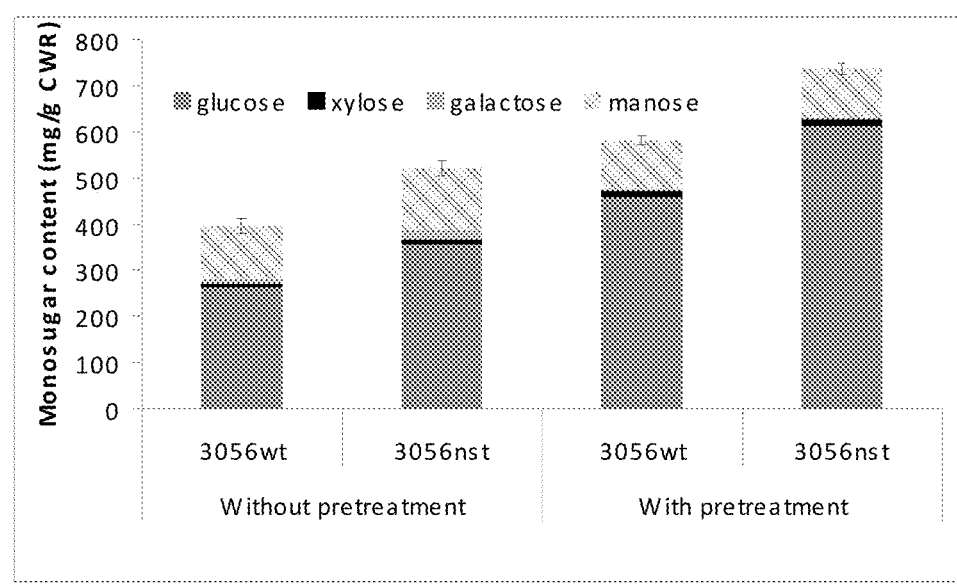
FIG. 5A-B

SEQUENCE LISTING

<160> NUMBER OF SEQ ID NOS: 9

<210> SEQ ID NO 1
<211> LENGTH: 960
<212> TYPE: DNA
<213> ORGANISM: Medicago truncatula

<400> SEQUENCE: 1

```
atgcctgata acatgagtat atctgttaat ggacaatctc aagttcctcc tggattccgg      60
tttcatccta ctgaagaaga gcttcttcaa tactacttga ggaaaaaagt ctcttatgag     120
aagattgacc ttgatgttat tcgtgatgtt gatctcaaca agcttgaacc atgggacatt     180
caagagaaat gcaaaatagg aacgactccg cagaatgatt ggtacttctt cagccataaa     240
gacaagaagt atccaaccgg aacaagaacc aatcgcgcta cggctgcagg gttctggaaa     300
gccaccggtc gtgacaaagt tatatatagt aatggaaaaa ggattggaat gagaaagact     360
cttgttttct acaaaggtcg tgctcctcat ggccaaaaat ctgattggat catgcatgag     420
tatagactcg acgataacac caccaatgac accaatctgg tgtcgaatat gattggtgat     480
ggtggtcaag aagaaggatg ggtggtgtgt aggatattca agaagaagaa tcatctcaaa     540
accctagaca gcccttctgg agagggaaga agaagccatc acttgtatga tacttgtgat     600
gaaggagctt tggagcaaat acttcaacaa atgggaaggg gttgcaagga agagaattat     660
gaagcaaatt acaataataa ttatggaagg tttgctaggc cttttgaatc tactctcaac     720
aacaatggtg gttataacaa tgaaaggttc atgaaacttc caaatttaga aagtccaaaa     780
tcaacaagca tggagaacaa tgagaacaac aatgatgggt atcatgcaat tattcaagta     840
gatatggcta atgaaaatga agggtcattc tctgatcatc atcatcatca tcatcataac     900
aacatggtta ataatccatt agaggcatca tcatcatcaa tggtgataag catgtggtga     960
```

<210> SEQ ID NO 2
<211> LENGTH: 1719
<212> TYPE: DNA
<213> ORGANISM: Populus

<400> SEQUENCE: 2

```
agctctgtaa atgttgtctc tcatttccgt ttctctttca tattgatctc tagctactct    60
ccttctctct tacatctaca ttgatcatat attttcgagc ctcgctgcct ataatgcctg   120
aggatatgat gaatctatca ataaatggtc agtctcaggt ccctccaggc tttagatttc   180
acccaacaga agaagagctt cttcactact acctcaggaa gaaagttgct aatgagaaga   240
tagaccttga tgtaattcgc gaggttgatc ttaataagct cgagccatgg gacatccaag   300
agaagtgcaa ataggatct acaccccaga atgattggta tttctttagt cacaaagaca   360
agaaatatcc cacagggact agaacaaatc gagctacggc tgctgggttt tggaaagcca   420
ctggccgtga taagatcatc tatagtgggt ttaaaagaat tggattgaga aagactcttg   480
tgttttacag aggaagagct ccacatggac agaaatccga ttggatcatg catgaatata   540
ggcttgatga caccaccaac gacactaatg tctcaaatcc tataggagag caatccctg    600
aagaagggtg ggtggtttgc cgggtattta gaaagaagaa ctatcaaaaa acccttgaga   660
gtcccaaaag ctcatcatgc tcattggatt caaaggctca tcagattctt ggttcaggaa   720
atgatggagt tcttgatcaa atacttctct atatgggaag gacttgcaag atggagaatg   780
aaacatttag caacatgaat atctccaaca acaacagtag tttaaggttt ctctcagaca   840
atagcatcag tgatgggctc catgaaagat tcatgcacct tcctcggcta gacagcccac   900
cactcccttc tattccaata agcagtccat cttttgatca agatcgaagt ttcaaatctt   960
gttatcacca atcgtacgat gagatgctga cagagaatga accttcctct tcaaaccaaa  1020
ttggcaatgg cactttcgac atgatctcat catccgtaat tcatggctcc aaatccgggc  1080
aacttaacga ttgggtaact cttgatcgtc tagtggcatc acaacttaat ggacatgaag  1140
cagagacatc caagcattta tcttgcttta ctaccggccc aaatgcgagt tttggtcttt  1200
ctcctgatga tgcacatgcaa ttatcacact tgcaaaattc tcatagatca tcatcaaaca  1260
ttcaagcaaa tacttctcat gtgtatacca acgagaatga cctatggggc ttcactaaat  1320
cttcgtctcc atcatcatca tcggacccat tatgccactt atcggtataa caaaagtgct  1380
caatattgta taccctatag agtaaatatag aaaccctaag agtctaggta cgtatacgtt  1440
atatagtagt ctttatgtat ctagtgcatg catgtattgc ataaataagc ttaaatttgg  1500
gtgatatata gttttagaa atatttgcga tgggatggca tagtcaattc acaccatttt  1560
gtaaatatcc taaataacga tatatgtcat ccattttatt caaaaattgt tatctaagaa  1620
tattacatct acagtttcat tttaactttc tgagtgattt gctcttccta cttgtaatca  1680
tatccaaagg tgattgaggt cttacctaaa taagtaacc                          1719
```

<210> SEQ ID NO 3
<211> LENGTH: 1338
<212> TYPE: DNA
<213> ORGANISM: Panicum virgatum

<400> SEQUENCE: 3

```
gggctctcca gcgggggcag cttcatgaac ccgtgcccgc ccagcacggt atcgatgggc    60
cggaggtacc tcggccccgc gccgccgccc tgcggcgaga ggacctgctc gtgctcctgc   120
ttgaacgacc tgcccatgta ctgcaggatc tggtcgagcg tgtcgtcgct ggaggagtac   180
tgcaggccgc ggtgcgccgc cgccgccgac ttgccgccgt cgcccactcg accgctgccg   240
tgcctgccgc cgcccccgct tcccgactct tgtggtggt gcttcttctt gaacacccctg   300
```

| | |
|---|---|
| cacaccaccc agccgtcctc ctggccggcg tccgacgacg cggcagcagc agcggcgacc | 360 |
| gtggcggcgg cgtcgtcgcc ggagacgacg gctcccgggt cgtcgaggcg gtactcgtgc | 420 |
| atgatccagt cggacttctg gccgtgcggg gcgcggccct tgtagaagac gagcgtcttg | 480 |
| cgcatgccga tgcgcttgac ggcgttgtag atggccttgt cgcggccggt ggccttccag | 540 |
| aagccggccg ccgtggcgcg gttcgtgcgc gtccccgtag ggtacttctt gtccttgtgg | 600 |
| ctgaagaagt accagtcgtt ctgccggccc gacccgatct tacatttctc ttggatgtcc | 660 |
| catggctcga gcttgttgag gtcgacgtcg cggatgacgt cgaggtcgat ctcctgggag | 720 |
| gcgaccttct tgcggaggta gtagttgagc agctcctcct ccgtggggtg gaaccggaac | 780 |
| cccggcggca cgcacgactg cccgttcacc gagatgctca ttatattgat tgatccctcg | 840 |
| ccggccggcc ggctcttcgt tctgtactct ctctctctct ctctctctct ctctctctct | 900 |
| ctctctctct ctctctctct ctctctctct ctctctctct ctctctctct ctctctctct | 960 |
| ctctctctct ctctggatac aggtggtgga gggctcaatt ggccggcgag ctggtggtga | 1020 |
| gtgtgtgtat agcagctgct agctagctag ctagctacag gtgagcgagg gagggaggga | 1080 |
| gggaggaaga cgacgatgag gtgagggata ggaggaggaa agagatcgat ggaagaagaa | 1140 |
| gctggtggca ggggaggaaa ggcgcgcact tttatagtgg gatgtggggg ggttgaggta | 1200 |
| cttgccgccc agcaaggcct agtgaaattt gggggatcat cgccttcgcg tcgtccatat | 1260 |
| gtccatgaat catattgcca tcattccatg ctagctgttg cctctctctc tctctctctc | 1320 |
| tgtatagcta tagcggct | 1338 |

<210> SEQ ID NO 4
<211> LENGTH: 1793
<212> TYPE: DNA
<213> ORGANISM: Oryza sativa

<400> SEQUENCE: 4

| | |
|---|---|
| aaaacggagg gaatatatta taagtaatga gatgctaata tatattttc tgtcctggac | 60 |
| aggtagtagg gttaattaat taattaaaca ttggatgcag acatgtttga cagtgccacc | 120 |
| ctaacttact actcgcattt gcctttaatc tctcttcttc ttcttttttc tcctccgtct | 180 |
| cttttgggctc cttaattttt cttttctttc tttctttctt ttctccagtg tctcactcac | 240 |
| taattaatta atcactcgat cttttgctaat cacctttgaa atatatcgat cgaatgatgt | 300 |
| ctctctatca gtatcattca tggtggatct ctctctctct ctctctctct tgcttttatt | 360 |
| ttttttttca cttacaattt tcttcttact tgtcttgtct ctgtaattac tgtactagca | 420 |
| gctagggtgg cagctcgagc gtacgtagcc tgacgtgtac gtatacgtgt acgtgtacgt | 480 |
| acagctacga atcatgtgtt acagtgccac gtggctgaga cgctctggcg tggccgacga | 540 |
| cggcggcggc ggcggcggtg gcggcgcagc cgaccgcgcg aagctccaca ggtcgtcgtc | 600 |
| ggtgccggcc ttggcaccgc cgagcagcct cgtggcggcg gcggagtagt aggcgaggcc | 660 |
| gtcgtcgtcg gcgcgtcga agcagagctg gtcgtcgggc gcgtcggagt tggcgccgtt | 720 |
| gaggtgcgac gcgacgaggc ggtccatcat ggcccagtcc gtgcggtggt ggtggtggag | 780 |
| cagcaggtgg tcgcggcgg ggggagctcg tgctcctgct tgcacgacct gcccatgtac | 840 |
| tgcaggatct ggtcgagcgc gtcgtcgctg gaggagtaag cgtgcgccgc cttggcgccg | 900 |
| gcgctgccgt cgccgccgtg cttgccgccg ccgccgccgg cctccttgtg gtggtgcttc | 960 |
| ttcttgaaca ccctgcacac cacccagcca tcctcctgcc cgccgtccgc cgccgccgcc | 1020 |
| atcgccgccg ccgcagcagc agcagaagta accgtgggtg tggcggcggc ggtgtcggtg | 1080 |

```
gcggggtcgt cgaggcggta ctcgtgcatg atccagtcgg acttctggcc gtggggggcg    1140
cggcccttgt agaagacgag cgtcttgcgc atgccaatgc ggtggacggc gttgtagatg    1200
gccttgtcgc ggccggtggc cttccagaac ccggccgccg tcgccctgtt cgtcctcgtc    1260
cccgtcgggt acttcttgtc cttgtggctg aagaagtacc agtcgttctg cggccctgac    1320
ccaatcttac acctctcttg gatgtcccat ggctcgagct tgttgaggtc gacgtcgcgg    1380
atgacgtcga ggtcgatctg ctcggaggcg accttcttgc ggaggtagta gttgagcagc    1440
tcctcctccg tcgggtggaa ccggaacccc ggcggcacgc acgactgccc gttcaccgag    1500
atgctcattg atgatcttct tcttcttctc cttcttgcta cctacctagc tgctcaatct    1560
cctcgctctt gctagctcta gcaacagcta gcttaattag cctcttcctt ccttctgata    1620
tatatgtata gatcgatcgt atagctagct agaaatggcg gctgcaggag aaggaagaag    1680
agattgagag gaggaggaag aagacgatcg agggcggtgg cgagggaaag gtgtggggtt    1740
tatatatagt tggggaggat ggatggatgc ttgattggga gaaggatgga cga           1793
```

<210> SEQ ID NO 5
<211> LENGTH: 1553
<212> TYPE: DNA
<213> ORGANISM: Sorghum bicolor

<400> SEQUENCE: 5

```
tcaccggctt cagctccggc tccggcagct gaatataatc acatcaccga tcattcattc     60
cctttgccta ctactactac tgctatctcc ttcaattctc ctgccatatc gatatatatc    120
aaatggcggt agtagtcgac gtctgaatca tcgtactctg atactacata cagacagacc    180
cacttcttct tcctccttgt tgctctagtt cctcttactc ttagctacag tagtagctgt    240
tagcttggct aatcgatcga tcgatcatga gcatctcggt gaacgggcag tcggtggtgc    300
cgccggggtt ccggttccac ccgacggagg aggagcttct gacctactac ctcaagaaga    360
aggtggcgtc ggagcgcatc gacctggacg tcatccgcga cgtcgacctg aacaagctcg    420
agccatggga catccaagag aagtgccgca tcggttctgg cccccagaac gactggtact    480
tcttcagcca caaggacaag aagtacccga cggggacgcg caccaaccgc gccaccgccg    540
ccggcttctg gaaggccacc ggccgcgaca aggccatcta cgcgtccggc gcccgccgca    600
tcggcatgcg caagacgctc gtcttctaca gggtcgtgc cccgcacggc cagaagtccg    660
actggatcat gcacgagtac cgcctcgagc cggcgctcga cgtcgacgcc gccgccggta    720
gtgcctccgc ccaccacgcc gccgccgggg ccgccgccga tcatcacccc tactacacct    780
cgtcgtcgcc gcctgctctt cctaccgcaa tccgtggcgc ggccggagac caacaagcgg    840
cgcaggagca ggaagggtgg gtgatctgca gggtgttcaa gaagaagaac ctcgttcacc    900
acggccagag cagcggcggc ggcgtgacag cagcaggatc caagatggcg tctgcggcgg    960
cgccatggga gggcagcccg agccactgct cgtcggtgac cgtcatcagt gaccacacca   1020
tgaacaagca ccaggcgcag gcgatgctgc agcactccgc cagcgacgac gacgcgctcg   1080
accacatcct gcagtacatg ggcggcggcg gcggcaagca gccggacacc aagccggtgc   1140
tgctggacca tcaccaccac caccacctag ctgcagcagc tactacgacg accaccgcgt   1200
gctctgccgg cggcgcgggt ctctacggga agttcatgaa gctcccgccc ctcgagcacg   1260
ccggcggcgg cggcgggctg ctgccagccc ctgcaggggc gtgcgactac ggcgccgccg   1320
acgcctcggg gatcgccgac tgggacgcgc tggaccggct cgccgcgtac gagctcaacg   1380
```

```
gcctctccga cgcgtccaag aacatgtccg ccttcttcga cgaacccagc gccaccgccg    1440
ccttctcctc ctcctcctcg tccgtgcacg cggccgccgt cgacggcgac ctgtggagcc    1500
tggcgaggtc ggtgtcggcg ttgcacgcgg acttgacgat gaacaacgtc tag           1553
```

```
<210> SEQ ID NO 6
<211> LENGTH: 319
<212> TYPE: PRT
<213> ORGANISM: Medicago truncatula

<400> SEQUENCE: 6
```

Met Pro Asp Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Ser Tyr Glu Lys Ile Asp Leu Asp Val Ile Arg
        35                  40                  45

Asp Val Asp Leu Asn Lys Leu Glu Pro Trp Asp Ile Gln Glu Lys Cys
    50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Asn Gly
            100                 105                 110

Lys Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
    130                 135                 140

Asp Asn Thr Thr Asn Asp Thr Asn Leu Val Ser Asn Met Ile Gly Asp
145                 150                 155                 160

Gly Gly Gln Glu Glu Gly Trp Val Val Cys Arg Ile Phe Lys Lys Lys
                165                 170                 175

Asn His Leu Lys Thr Leu Asp Ser Pro Ser Gly Glu Gly Arg Arg Ser
            180                 185                 190

His His Leu Tyr Asp Thr Cys Asp Glu Gly Ala Leu Glu Gln Ile Leu
        195                 200                 205

Gln Gln Met Gly Arg Gly Cys Lys Glu Glu Asn Tyr Glu Ala Asn Tyr
    210                 215                 220

Asn Asn Asn Tyr Gly Arg Phe Ala Arg Pro Phe Glu Ser Thr Leu Asn
225                 230                 235                 240

Asn Asn Gly Gly Tyr Asn Asn Glu Arg Phe Met Lys Leu Pro Asn Leu
                245                 250                 255

Glu Ser Pro Lys Ser Thr Ser Met Glu Asn Asn Glu Asn Asn Asp
            260                 265                 270

Gly Tyr His Ala Ile Ile Gln Val Asp Met Ala Asn Glu Asn Glu Gly
        275                 280                 285

Ser Phe Ser Asp His His His His His Asn Asn Met Val Asn
    290                 295                 300

Asn Pro Leu Glu Ala Ser Ser Ser Met Val Ile Ser Met Trp
305                 310                 315

```
<210> SEQ ID NO 7
<211> LENGTH: 365
<212> TYPE: PRT
<213> ORGANISM: Arabidopsis thaliana
```

<400> SEQUENCE: 7

```
Met Met Ser Lys Ser Met Ser Ile Ser Val Asn Gly Gln Ser Gln Val
1               5                   10                  15

Pro Pro Gly Phe Arg Phe His Pro Thr Glu Glu Leu Leu Gln Tyr
            20                  25                  30

Tyr Leu Arg Lys Lys Val Asn Ser Ile Glu Ile Asp Leu Asp Val Ile
        35                  40                  45

Arg Asp Val Asp Leu Asn Lys Leu Glu Pro Trp Asp Ile Gln Glu Met
50                  55                  60

Cys Lys Ile Gly Thr Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Ala
                85                  90                  95

Ala Gly Phe Trp Lys Ala Thr Gly Arg Asp Lys Ile Ile Tyr Ser Asn
            100                 105                 110

Gly Arg Arg Ile Gly Met Arg Lys Thr Leu Val Phe Tyr Lys Gly Arg
        115                 120                 125

Ala Pro His Gly Gln Lys Ser Asp Trp Ile Met His Glu Tyr Arg Leu
130                 135                 140

Asp Asp Asn Ile Ile Ser Pro Glu Asp Val Thr Val His Glu Val Val
145                 150                 155                 160

Ser Ile Ile Gly Glu Ala Ser Gln Asp Glu Gly Trp Val Val Cys Arg
                165                 170                 175

Ile Phe Lys Lys Lys Asn Leu His Lys Thr Leu Asn Ser Pro Val Gly
            180                 185                 190

Gly Ala Ser Leu Ser Gly Gly Gly Asp Thr Pro Lys Thr Thr Ser Ser
        195                 200                 205

Gln Ile Phe Asn Glu Asp Thr Leu Asp Gln Phe Leu Glu Leu Met Gly
210                 215                 220

Arg Ser Cys Lys Glu Glu Leu Asn Leu Asp Pro Phe Met Lys Leu Pro
225                 230                 235                 240

Asn Leu Glu Ser Pro Asn Ser Gln Ala Ile Asn Asn Cys His Val Ser
                245                 250                 255

Ser Pro Asp Thr Asn His Asn Ile His Val Ser Asn Val Val Asp Thr
            260                 265                 270

Ser Phe Val Thr Ser Trp Ala Ala Leu Asp Arg Leu Val Ala Ser Gln
        275                 280                 285

Leu Asn Gly Pro Thr Ser Tyr Ser Ile Thr Ala Val Asn Glu Ser His
290                 295                 300

Val Gly His Asp His Leu Ala Leu Pro Ser Val Arg Ser Pro Tyr Pro
305                 310                 315                 320

Ser Leu Asn Arg Ser Ala Ser Tyr His Ala Gly Leu Thr Gln Glu Tyr
                325                 330                 335

Thr Pro Glu Met Glu Leu Trp Asn Thr Thr Thr Ser Ser Leu Ser Ser
            340                 345                 350

Ser Pro Gly Pro Phe Cys His Val Ser Asn Gly Ser Gly
        355                 360                 365

<210> SEQ ID NO 8
<211> LENGTH: 334
<212> TYPE: PRT
<213> ORGANISM: Arabidopsis thaliana

<400> SEQUENCE: 8
```

Met Asn Ile Ser Val Asn Gly Gln Ser Gln Val Pro Pro Gly Phe Arg
1               5                   10                  15

Phe His Pro Thr Glu Glu Leu Leu Lys Tyr Tyr Leu Arg Lys Lys
            20                  25                  30

Ile Ser Asn Ile Lys Ile Asp Leu Asp Val Ile Pro Asp Ile Asp Leu
            35                  40                  45

Asn Lys Leu Glu Pro Trp Asp Ile Gln Glu Met Cys Lys Ile Gly Thr
        50                  55                  60

Thr Pro Gln Asn Asp Trp Tyr Phe Tyr Ser His Lys Asp Lys Lys Tyr
65                  70                  75                  80

Pro Thr Gly Thr Arg Thr Asn Arg Ala Thr Thr Val Gly Phe Trp Lys
                85                  90                  95

Ala Thr Gly Arg Asp Lys Thr Ile Tyr Thr Asn Gly Asp Arg Ile Gly
            100                 105                 110

Met Arg Lys Thr Leu Val Phe Tyr Lys Gly Arg Ala Pro His Gly Gln
            115                 120                 125

Lys Ser Asp Trp Ile Met His Glu Tyr Arg Leu Asp Glu Ser Val Leu
130                 135                 140

Ile Ser Ser Cys Gly Asp His Asp Val Asn Val Glu Thr Cys Asp Val
145                 150                 155                 160

Ile Gly Ser Asp Glu Gly Trp Val Val Cys Arg Val Phe Lys Lys Asn
                165                 170                 175

Asn Leu Cys Lys Asn Met Ile Ser Ser Pro Ala Ser Ser Val Lys
            180                 185                 190

Thr Pro Ser Phe Asn Glu Glu Thr Ile Glu Gln Leu Leu Glu Val Met
                195                 200                 205

Gly Gln Ser Cys Lys Gly Glu Ile Val Leu Asp Pro Phe Leu Lys Leu
210                 215                 220

Pro Asn Leu Glu Cys His Asn Asn Thr Thr Ile Thr Ser Tyr Gln Trp
225                 230                 235                 240

Leu Ile Asp Asp Gln Val Asn Asn Cys His Val Ser Lys Val Met Asp
                245                 250                 255

Pro Ser Phe Ile Thr Ser Trp Ala Ala Leu Asp Arg Leu Val Ala Ser
            260                 265                 270

Gln Leu Asn Gly Pro Asn Ser Tyr Ser Ile Pro Ala Val Asn Glu Thr
        275                 280                 285

Ser Gln Ser Pro Tyr His Gly Leu Asn Arg Ser Gly Cys Asn Thr Gly
    290                 295                 300

Leu Thr Pro Asp Tyr Tyr Ile Pro Glu Ile Asp Leu Trp Asn Glu Ala
305                 310                 315                 320

Asp Phe Ala Arg Thr Thr Cys His Leu Leu Asn Gly Ser Gly
                325                 330

<210> SEQ ID NO 9
<211> LENGTH: 358
<212> TYPE: PRT
<213> ORGANISM: Arabidopsis thaliana

<400> SEQUENCE: 9

Met Ala Asp Asn Lys Val Asn Leu Ser Ile Asn Gly Gln Ser Lys Val
1               5                   10                  15

Pro Pro Gly Phe Arg Phe His Pro Thr Glu Glu Leu Leu His Tyr
            20                  25                  30

Tyr Leu Arg Lys Lys Val Asn Ser Gln Lys Ile Asp Leu Asp Val Ile

-continued

```
            35                  40                  45
Arg Glu Val Asp Leu Asn Lys Leu Glu Pro Trp Asp Ile Gln Glu Glu
        50                  55                  60
Cys Arg Ile Gly Ser Thr Pro Gln Asn Asp Trp Tyr Phe Phe Ser His
65                  70                  75                  80
Lys Asp Lys Lys Tyr Pro Thr Gly Thr Arg Thr Asn Arg Ala Thr Val
                85                  90                  95
Ala Gly Phe Trp Lys Ala Thr Gly Arg Asp Lys Ile Ile Cys Ser Cys
               100                 105                 110
Val Arg Arg Ile Gly Leu Arg Lys Thr Leu Val Phe Tyr Lys Gly Arg
           115                 120                 125
Ala Pro His Gly Gln Lys Ser Asp Trp Ile Met His Glu Tyr Arg Leu
       130                 135                 140
Asp Asp Thr Pro Met Ser Asn Gly Tyr Ala Asp Val Val Thr Glu Asp
145                 150                 155                 160
Pro Met Ser Tyr Asn Glu Glu Gly Trp Val Val Cys Arg Val Phe Arg
               165                 170                 175
Lys Lys Asn Tyr Gln Lys Ile Asp Asp Cys Pro Lys Ile Thr Leu Ser
               180                 185                 190
Ser Leu Pro Asp Asp Thr Glu Glu Glu Lys Gly Pro Thr Phe His Asn
           195                 200                 205
Thr Gln Asn Val Thr Gly Leu Asp His Val Leu Leu Tyr Met Asp Arg
       210                 215                 220
Thr Gly Ser Asn Ile Cys Met Pro Glu Ser Gln Thr Thr Thr Gln His
225                 230                 235                 240
Gln Asp Asp Val Leu Phe Met Gln Leu Pro Ser Leu Glu Thr Pro Lys
               245                 250                 255
Ser Glu Ser Pro Val Asp Gln Ser Phe Leu Thr Pro Ser Lys Leu Asp
           260                 265                 270
Phe Ser Pro Val Gln Glu Lys Ile Thr Glu Arg Pro Val Cys Ser Asn
       275                 280                 285
Trp Ala Ser Leu Asp Arg Leu Val Ala Trp Gln Leu Asn Asn Gly His
    290                 295                 300
His Asn Pro Cys His Arg Lys Ser Phe Asp Glu Glu Glu Glu Asn Gly
305                 310                 315                 320
Asp Thr Met Met Gln Arg Trp Asp Leu His Trp Asn Asn Asp Asp Asn
               325                 330                 335
Val Asp Leu Trp Ser Ser Phe Thr Glu Ser Ser Ser Leu Asp Pro
           340                 345                 350
Leu Leu His Leu Ser Val
       355
```

PLANTS WITH MODIFIED LIGNIN CONTENT AND METHODS FOR PRODUCTION THEREOF

This application claims the priority of U.S. Provisional Application Ser. No. 61/225,126, filed Jul. 13, 2009, the entire disclosure of which is incorporated herein by reference.

This invention was made with Government support under DE-FG02-06ER64303 awarded by the U.S. Department of Energy. The Government has certain rights in the invention.

BACKGROUND OF THE INVENTION

1. Field of the Invention

The present invention relates generally to the field of agriculture and plant genetics. More particularly, it concerns genetically modified plants comprising reduced lignin content.

2. Description of Related Art

Ethanol is increasingly being considered as a renewable, cleaner alternative to petroleum based fuels. Ethanol may also be produced from sugars and starches as well as from lignocellulosic based biomass which constitute the most abundant biomass on earth. While energy conversion from lignocellulosic biomass is less efficient, it does not require crops used for human food production (e.g., corn) to be used as feed stock.

The principal source of fermentable sugar in lignocellulosic biomass is cellulose. In typical lignocellulosic biomass used for ethanol production, cellulose accounts for between 35 to 50% of the mass. Cellulose is a long chain polysaccharide carbohydrate, composed of repeating cellobiose (β-1,4 glucose disaccharide) units. Hemicellulose also contributes to the fermentable sugar content of lignocellulosic biomass. It comprises about 20 to 35% of lignocellulosic biomass mass, and is a mixture of a variety of sugars including arabinose, galactose, glucose, mannose, and xylose, and derivatives of such sugars.

The third major component of lignocellulosic biomass, lignin, is not a sugar based fermentable polymer. Lignin is a complex polymer of hydroxylated and methoxylated phenylpropane units, linked via oxidative coupling and comprises about 12 to 20% of lignocellulosic biomass. For ethanol production from lignocellulosic biomass, the cellulose and hemicellulose components are processed to produce their constituent sugars, and these sugars are then used to make ethanol via fermentation. However, lignin does not contribute fermentable sugar to lignocellulosic biomass, and its presence reduces the efficiency of enzymatic hydrolysis of cellulose, apparently by physically shielding the cellulose molecules from the hydrolytic enzymes. Consequently, chemical loosening of lignin from the lignocellulosic biomass is often one of the first steps in the ethanol production processes. This process consumes energy, and utilizes chemical treatments (e.g., hot acid) that require clean-up (e.g., neutralization and disposal of waste).

Genetic modifications necessary to achieve reduced lignin content and improved cellulose and/or hemicellulose availability for saccharification were not clear based on currently available information. Development of plants with modified cell wall composition would have a significant benefit for the production of ethanol from plants and could potentially have a broad range of other beneficial applications.

SUMMARY OF THE INVENTION

In a first embodiment there is provided a plant comprising a down-regulates NST transcription factor wherein the plant exhibits reduced lignin content. As used herein, the term NST transcription factor refers to a polypeptide encoded by the NST1 gene from *M. truncatula* (MtNST1) and homologs thereof. For example, a homolog may be defined as a gene encoding a polypeptide having a C-terminal region corresponding to the MtNST1 C-terminal region (e.g., having at least 60%, 70%, 80%, 85%, 90%, 95%, 98% or greater amino acid identity over positions 190 to 317 of the MtNST1 polypeptide, SEQ ID NO: 6). In certain aspects, a homolog gene may be defined as a gene encoding a polypeptide having at least about 60%, 70%, 80%, 85%, 90%, 95%, 98% or higher identity to the full-length polypeptide encoded by MtNST1 (SEQ ID NO: 6).

In one embodiment, a selected DNA that down-regulates an NST transcription factor may be defined as a genomic NST gene comprising a mutation that disrupts the gene by down-regulating NST expression, by abrogating expression entirely or by rendering the gene product non-functional. For example, the mutation may be a point mutation, an insertion or a deletion and the mutation may be located in a coding (e.g., in an NST exon, such as exons 1, 2 or 3) or non-coding portion to the NST gene (e.g., in the NST promoter region). Mutations in an NST gene can be accomplished by any of the methods well known to those in the art including random mutagenesis methods such as irradiation, random DNA integration (e.g., via a transposon) or by using a chemical mutagen. Moreover, in certain aspects, a NST gene may be mutated using a site-directed mutagenesis approach such as by using homologous recombination vector. Further detailed methods for inducing a mutations in plant genes are provided below.

In a further embodiment, a selected DNA that down-regulates an NST transcription factor comprises a DNA molecule capable of expressing a nucleic acid sequence complementary to all or a portion of a NST gene sequence or a NST messenger RNA (mRNA). Thus, in some aspects, a transgenic plant may comprise an antisense, RNAi or miRNA construct for down-regulation of NST. For example, a transgenic plant can comprise a promoter which expresses a sequence complimentary to all or a portion of a NST sequence from the plant. In certain specific embodiments, a transgenic plant comprises a nucleic acid molecule capable of expressing an nucleic acid sequence complementary to all or a portion of a *Medicago* NST (SEQ ID NO: 1), a Poplar NST (SEQ ID NO: 2), a switchgrass NST (SEQ ID NO: 3), a rice NST (SEQ ID NO: 4) or a sorghum NST (SEQ ID NO: 5) nucleic acid sequence. Moreover, in certain aspects, the selected DNA that down regulates NST may comprise a tissue specific or inducible promoter operably linked to the nucleic acid sequence complimentary to all or part of a plant NST gene or mRNA. In some cases, the promoter sequence is selected from the group consisting of a developmentally-regulated, organelle-specific, inducible, tissue-specific, constitutive, cell-specific, seed specific, or germination-specific promoter.

In still further aspects, a transgenic plant further comprises a second DNA sequence that down-regulates lignin biosynthesis. For example, in certain embodiments, the second DNA sequence down regulates a lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl coA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH). In certain aspects, the second DNA comprises a mutated genomic copy of one or more lignin biosynthesis gene that disrupts expression of the gene or the function of the gene product. In still further aspects, a transgenic plant may further comprise a selected DNA that is an antisense or RNAi construct comprising an expressible nucleic acid sequence complimentary to all or part of a lignin biosynthesis gene. In certain embodiments, at least two, at least three, or at least four additional lignin biosynthesis genes are down-regulated.

A variety of plants can be modified in accordance with the instant disclosure. For example, in some aspects, a plant comprising a down-regulated NST transcription factor may be a forage plant, a biofuel crop, a cereal crop or an industrial plant. For example, a forage plant may be a forage soybean, alfalfa, clover, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass or reed canarygrass plant. In certain aspects, a plant is a biofuel crop including, but not limited to, switchgrass (*Panicum virgatum*), giant reed (*Arundo donax*), reed canarygrass (*Phalaris arundinacea*), *Miscanthus×giganteus, Miscanthus* sp., sericea lespedeza (*Lespedeza cuneata*), corn, sugarcane, sorghum, millet, ryegrass (*Lolium multiflorum, Lolium* sp.), timothy, Kochia (*Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass or poplar. Cereal crops for use according to the instant disclose include, but are not limited to, maize, rice, wheat, barley, sorghum, millet, oat, rye, triticle, buckwheat, fonio (*Digitaria* sp.) or quinoa. In certain embodiments, the plant may be defined as a *Medicago*, poplar, switchgrass, rice or sorghum plant having a NST coding region of SEQ ID NO: 1, SEQ ID NO: 2, SEQ ID NO: 3, SEQ ID NO: 4 and SEQ ID NO: 5, respectively.

In still further aspects there is provided a part of a plant described herein such as a protoplast, cell, meristem, root, pistil, anther, flower, seed, embryo, stalk or petiole.

In another embodiment, a transgenic or mutated plant produced herein may be further defined as an R0 plant, or as a progeny plant of any generation of an R0 plant, wherein the plant has inherited the selected DNA or mutation from the R0 plant. Moreover, in certain aspects, the a progeny plant as described herein may be defined as a progeny plant that has bee crossed with a second plant, such as a variety with reduced lodging In other embodiments, the invention comprises a seed of a plant wherein the seed comprises a mutation or selected DNA that down-regulates a NST transcription factor. A transgenic cell of such a plant also comprises an embodiment of the invention.

In still a further embodiment, there is provided a nucleic acid molecule comprising a nucleic acid sequence selected from the group consisting of: (a) a nucleic acid sequence that hybridizes to the nucleic acid sequence of SEQ ID NO: 1; SEQ ID NO: 2; SEQ ID NO: 3; SEQ ID NO: 4 or SEQ ID NO: 5 under conditions of 1×SSC at 65° C.; (b) a nucleic acid sequence complimentary to the nucleic acid sequence of SEQ ID NO: 1; SEQ ID NO: 2; SEQ ID NO: 3; SEQ ID NO: 4 or SEQ ID NO: 5; and (c) a nucleic acid sequence having at least 80% sequence identity to the full compliment of the nucleic acid sequence of SEQ ID NO: 1; SEQ ID NO: 2; SEQ ID NO: 3; SEQ ID NO: 4 or SEQ ID NO: 5, wherein the nucleic acid sequence is operably linked to a promoter sequence and wherein expression of the DNA molecule in a plant cell down-regulates NST expression. In some aspects, a DNA molecule provided comprises a nucleic acid sequence having at least 85%, 90%, 95%, 96%, 97%, 98% or 99% sequence identity to the full compliment of the nucleic acid sequence of SEQ ID NO: 1; SEQ ID NO: 2; SEQ ID NO: 3; SEQ ID NO: 4 or SEQ ID NO: 5.

In still further aspects there is provided a nucleic acid molecule comprising a nucleic acid sequence selected from the group consisting of: (a) a nucleic acid sequence that hybridizes to the nucleic acid sequence complementary to the sequence of SEQ ID NO: 1; SEQ ID NO: 2; SEQ ID NO: 3; SEQ ID NO: 4 or SEQ ID NO: 5 under conditions of 1×SSC and 65° C.; (b) a nucleic acid comprising the sequence of SEQ ID NO: 1; SEQ ID NO: 2; SEQ ID NO: 3; SEQ ID NO: 4 or SEQ ID NO: 5; and (c) a nucleic acid sequence having at least 80% sequence identity to the nucleic acid sequence of SEQ ID NO: 1; SEQ ID NO: 2; SEQ ID NO: 3; SEQ ID NO: 4 or SEQ ID NO: 5; wherein the nucleic acid sequence is operable linked to a heterologous promoter sequence and wherein expression of the DNA molecule in a plant cell modulates the lignin content of said plant cell. In some aspects, a DNA molecule provided comprises (c) a nucleic acid sequence having at least 85%, 90%, 95%, 96%, 97%, 98% or 99% sequence identity to the nucleic acid sequence of SEQ ID NO: 1; SEQ ID NO: 2; SEQ ID NO: 3; SEQ ID NO: 4 or SEQ ID NO: 5. Thus, in certain aspects a nucleic acid molecule provided herein may be defined as nucleic acid molecule capable of expressing a functional NST transcription factor and thereby increasing lignin content in a plant. Conversely, in certain aspects a nucleic acid molecule comprises a nucleic acid sequence comprising a compliment of (a)-(c) operable linked to a promoter sequence. Such a nucleic acid molecule may, in certain cases, be used to down-regulate an NST gene and thereby reduce lignin content in a plant expressing the nucleic acid sequence.

In further embodiments a transgenic plant, plant part or plant cell comprising a nucleic acid molecule as described herein is provided. For example, in certain aspects, nucleic acid molecules are provided that down-regulate NST. Plants and plant parts comprising a down-regulated NST may, in certain aspects, be defined as comprising decreased lignin content and increased fermentable carbohydrate content. In certain aspects, such plants may be used as feedstock for biofuel production.

In yet a further embodiment, there is provided a method of increasing the level or availability of one or more fermentable carbohydrates in a biofuel crop species plant comprising down-regulating an NST transcription factor in the plant. Thus, in certain aspects, a plant described herein may be defined as comprising an increased level of available carbohydrates, such as an increased level of available glucose.

Moreover, there is provided herein a method of decreasing the lignin (e.g., a S or G lignin) content in a plant comprising down-regulating an NST transcription factor in the plant. Thus, in certain aspects a plant provided here may be defined as having a reduced lignin content relative to a wild-type counterpart. Moreover, in certain aspects a plant may be defined as having a reduced G lignin content or a reduced or undetectable S lignin content. Plants provided herein comprising reduced lignin content may, in certain aspects, be used in the manufacture of biofuel feedstock (e.g., ethanol and biodiesel) or paper pulp materials.

In still a further embodiment, there is provided a method for increasing the digestibility of a forage crop comprising down-regulating an NST transcription factor in the plant. For example, in certain aspects, plants described herein comprise reduced lignin content and have enhanced digestibility. In some cases such plants or parts thereof may be used for livestock forage or in the manufacture of a livestock feed.

In still a further aspect, the instant disclosure provides a method of decreasing the transpiration rate and/or increasing the drought tolerance of a plant comprising down-regulating an NST transcription factor in the plant.

In yet a further aspect, the instant disclosure provides a method of decreasing the male fertility of a plant comprising down-regulating an NST transcription factor in the plant.

In yet a further embodiment, there is provided a method of increasing the lignin content of a plant comprising expressing a nucleic acid molecule in a plant comprising the coding sequence for an NST transcription factor. Thus, in certain aspects, transgenic plants comprising increased lignin content are provided.

In still a further embodiment, there is provided a method for the manufacture of a commercial product comprising obtaining a plant or plant part comprising a mutation or a selected DNA that down-regulates a NST transcription factor and producing a commercial product therefrom. For example, a plant or plant part described herein can be manufactured into a products such as, paper, paper pulp, ethanol, biodiesel, silage, animal feed or fermentable biofuel feedstock.

In yet another aspect, the invention provides a method of producing ethanol comprising: (a) obtaining a plant of a biofuel crop species comprising a selected DNA that down-regulates a NST transcription factor in the plant wherein the plant exhibits an increase in fermentable carbohydrates relative to a plant of the same genotype lacking the selected DNA; (b) treating tissue from the plant to render carbohydrates in the tissue fermentable; and (c) fermenting the carbohydrates to produce ethanol.

In yet another aspect, the invention provides a method for processing lignocellulosic biomass from a plant or plant part described herein. In one embodiment the method for processing lignocellulosic biomass from a plant or plant part, may comprise acid and/or enzymatic treatment(s). The enzymatic treatment may comprise treatment with one or more cellulolytic enzymes, such as a cellulase. In another embodiment, the method comprises an acid treatment prior to or during a treatment to render carbohydrates in the plant fermentable. In yet another embodiment, no acid treatment is performed.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-B: Alignments between *Arabidopsis* and *M. truncatula* NST polypeptide sequences. FIG. 1A, Alignment between *Arabidopsis* NST1 (SEQ ID NO: 7), NST2 (SEQ ID NO: 8) and *M. truncatula* NST1 (SEQ ID NO: 6). FIG. 1B, Alignment between *Arabidopsis* NST1 (SEQ ID NO: 7), NST3 (SEQ ID NO: 9) and *M. truncatula* NST1 (SEQ ID NO: 6). Black shading indicates identical amino acids.

FIG. 2A-B: Characterization of MtNST1. FIG. 2A, Schematic diagram of the structure of the MtNST1 gene and the positions of Tnt1 retrotransposon insertions in the NST1-1 (NF3056), NST1-2 (NF2911), NST1-3 (NF4041) and NST1-4 (NF3687) lines. Numbers indicate nucleotide positions from the site of initiation of translation. Boxes represent exons. FIG. 2B, RT-PCR analysis of MtNST1 transcripts in Tnt-insertion lines. Actin was used as loading control. 1 and 3, wild-type; 2, NST1-1; 4 NST1-2.

FIG. 3A-D: Cell wall composition of wild type and NST1-1. FIG. 3A, AcBr lignin content of the stems (internodes 5-8). n=10. FIG. 3B, Thioacidolysis yields of individual lignin monomers from cell walls of stem of wild-type (1-3) and NST1-1 (4-6). FIG. 3C, Total sugar content of cell walls from stems of wild-type and NST1-1. n=6. FIG. 3D, Monosaccharide composition of stems (internodes 5-8) from wild-type (1-3) and NST1-1 (4-6). Data are means of duplicate assays. CWR, cell wall residue. The bars are mean and standard deviation for 10 (FIG. 3A) or 6 (FIG. 3C) biological replicates.

FIG. 4A-D: Levels of cell wall biosynthetic gene transcripts in wild-type and NST1-1, as determined by qRT-PCR. FIG. 4A, qRT-PCR analysis of NST1 and lignin pathway gene transcripts in *M. truncatula* stem internodes at different developmental stages (from 50 day-old plants). 1=internode 2, 2=internode 3, 3=internode 5. Transcript level is expressed relative to actin. FIG. 4B, Expression of genes related to lignin biosynthesis. 1 and 4, NST1-1; 2 and 3, wild-type. Data are means and SDs of triplicate assays. FIGS. 4C, D, Expression of putative IRX1 and FRA8 genes. Transcript levels were measured with three different primer pairs. Data are means and SDs of triplicate assays. 1 and 2, wild-type; 3 and 4, NST1-1.

FIG. 5A-B: Sugar release from cell walls of wild-type *M. truncatula* and the NST1-1 mutant by chemical and enzymatic saccharification. FIG. 5A, Saccharification efficiencies after dilute acid pretreatment. FIG. 5B, Enzymatic saccharification efficiencies with and without acid pretreatment.

DESCRIPTION OF ILLUSTRATIVE EMBODIMENTS

A major stumbling block to the use of lignocellulosic biomass for production fuels is the difficulty in accessing cell wall carbohydrates that store a large portion of the solar energy converted by the plant Likewise, plant cell wall components are difficult for animals to digest and thus are not able to be efficiently converted into animal mass for human food (e.g., in grazing livestock). Much effort has been focused on genetic modification of plants to improve digestibility and energy yield for biofuel from cell wall components. However, these efforts have been stymied by the fact that genes encoding the enzymes involved in cell wall synthesis are highly redundant. For example, 10 cellulose synthase genes are present in *Arabidopsis* and poplar has 18 such genes (Djerbi et al., 2005; Keegstra and Walton, 2006) Likewise, at least 9 cinnamyl alcohol dehydrogenase (CAD) enzymes catalyzing reduction of various phenylpropenyl aldehyde derivatives in lignin biosynthesis have been shown to have enzyme activity in *Arabidopsis* (Kim et al., 2004). Even transcription factors that are involved in some aspects of cell wall synthesis have proven to be redundant. *Arabidopsis*, for example, contains three partially redundant NST transcription genes. In view of previous work it seemed that a wide array of genetic modifications would be necessary to affect major changes in plant cell wall composition.

The studies provided herein surprisingly demonstrate that an NST transcription factor gene, such as the *M. truncatula* NST, plays a primary regulatory role in controlling cell wall composition. Plants with mutations in the *M. truncatula* NST1 gene exhibit severe secondary wall biosynthesis defects including reduced lignin content. Moreover, mutant plants exhibit the loss of fluorescence from the guard cell walls indicating that NST1 also controls modification of primary cell walls in guard cells. Further investigation identified a variety of genes that are subject to NST regulation (see, e.g., Table 1 below). Mutation of NST1 in *M. truncatula* resulted not only in the abolition of lignification in interfascular fibers, but significantly reduced xylose and increased glucose levels upon extraction of sugars from the plants. The overall consequence of these changes in cell wall composition is that the mutant plants are more amenable to chemical and enzymatic treatment for release of sugars for ethanol fermentation. Whereas the lower amount of xylose in the pretreatment hydrolysate is likely due to impaired biosynthesis of hemicelluloses in NST1 mutants, the increased glucose content may be due to decreased crystallinity of cellulose. Knockout of NST1 in *M. truncatula* greatly improved the enzymatic hydrolysis efficiency of biomass with or without acid pretreatment. Although there is an overall reduction in cell wall polysaccharide in the NST mutants, this was more than compensated for as regards saccharification by the reduction in lignin content. Furthermore, the growth reductions observed in lines harboring a complete knock-out of NST1 are significantly less than observed in transgenic plants in which saccharification efficiency is similarly improved through the knock-down of monolignol biosynthetic enzymes (Chen and Dixon, 2007).

Reduction in lignin levels also directly impacts forage digestibility in a parallel manner to the effects on enzymatic saccharifciation (Reddy et al., 2005; Chen and Dixon, 2007). Thus, forage plants down-regulated in NST1 would be expected to exhibit improved digestibility. At the same time, NST1 down-regulated plants exhibit a higher leaf to stem ratio than wild-type plants, another trait that is advantageous for a forage crop. Moreover, NST mutated plants are also less likely to spread in natural environments without human intervention due to the impairment of anther dehiscence and resultant reduced pollen flow. Thus, the methods overcome the previous inability to alter global cell wall composition in the plants. The provided transgenic plants comprise a variety of traits that are useful in the production of agricultural products and could previously have been realized.

I. PRODUCTION OF ETHANOL FROM LIGNOCELLULOSIC BIOMASS

The overall process for the production of ethanol from biomass typically involves two steps: saccharification and fermentation. First, saccharification produces fermentable sugars from the cellulose and hemicellulose in the lignocellulosic biomass. Second, those sugars are then fermented to produce ethanol. Thorough, detailed discussion of additional methods and protocols for the production of ethanol from biomass are reviewed in Wyman (1999); Gong et al., (1999); Sun and Cheng, (2002); and Olsson and Hahn-Hagerdal (1996).

A. Pretreatment

Raw biomass is typically pretreated to increase porosity, hydrolyze hemicellulose, remove lignin and reduce cellulose crystallinity, all in order to improve recovery of fermentable sugars from the cellulose polymer. As a preliminary step in pretreatment, the lignocellulosic material may be chipped or ground. The size of the biomass particles after chipping or grinding is typically between 0.2 and 30 mm. After chipping a number of other pretreatment options may be used to further prepare the biomass for saccharification and fermentation, including steam explosion, ammonia fiber explosion, acid hydrolysis.

1. Steam Explosion

Steam explosion is a very common method for pretreatment of lignocellulosic biomass and increases the amount of cellulose available for enzymatic hydrolysis (U.S. Pat. No. 4,461,648). Generally, the material is treated with high-pressure saturated steam and the pressure is rapidly reduced, causing the materials to undergo an explosive decompression. Steam explosion is typically initiated at a temperature of 160-260° C. for several seconds to several minutes at pressures of up to 4.5 to 5 MPa. The biomass is then exposed to atmospheric pressure. The process causes hemicellulose degradation and lignin transformation. Addition of $H_2SO_4$, $SO_2$, or $CO_2$ to the steam explosion reaction can improve subsequent cellulose hydrolysis, decrease production of inhibitory compounds and lead to the more complete removal of hemicellulose (Morjanoff and Gray, 1987).

2. Ammonia Fiber Explosion (AFEX)

In AFEX pretreatment, the biomass is treated with approximately 1-2 kg ammonia per kg dry biomass for approximately 30 minutes at pressures of 1.5 to 2 MPa. (U.S. Pat. No. 4,600,590; U.S. Pat. No. 5,037,663; Mes-Hartree, et al., 1988). Like steam explosion, the pressure is then rapidly reduced to atmospheric levels, boiling the ammonia and exploding the lignocellulosic material. AFEX pretreatment appears to be especially effective for biomass with a relatively low lignin content, but not for biomass with high lignin content such as newspaper or aspen chips (Sun and Cheng, 2002).

3. Acid Hydrolysis

Concentrated or dilute acids may also be used for pretreatment of lignocellulosic biomass. $H_2SO_4$ and HCl have been used at high, >70%, concentrations. In addition to pretreatment, concentrated acid may also be used for hydrolysis of cellulose (U.S. Pat. No. 5,972,118). Dilute acids can be used at either high (>160° C.) or low (<160° C.) temperatures, although high temperature is preferred for cellulose hydrolysis (Sun and Cheng, 2002). $H_2SO_4$ and HCl at concentrations of 0.3 to 2% (w/w) and treatment times ranging from minutes to 2 hours or longer can be used for dilute acid pretreatment.

Other pretreatments include alkaline hydrolysis, oxidative delignification, organosolv process, or biological pretreatment; see Sun and Cheng (2002).

B. Saccharification

After pretreatment, the cellulose in the lignocellulosic biomass may be hydrolyzed with cellulase enzymes. Cellulase catalyzes the breakdown of cellulose to release glucose which can then be fermented into ethanol.

Bacteria and fungi produce cellulases suitable for use in ethanol production (Duff and Murray, 1995). For example, *Cellulomonas fimi* and *Thermomonospora fusca* have been extensively studied for cellulase production. Among fungi, members of the *Trichoderma* genus, and in particular *Trichoderma reesi*, have been the most extensively studied. Numerous cellulases are available from commercial sources as well. Cellulases are usually actually a mixture of several different specific activities. First, endoglucanases create free chain ends of the cellulose fiber. Exoglucanases remove cellobiose units from the free chain ends and beta-glucosidase hydrolyzes cellobiose to produce free glucose.

Reaction conditions for enzymatic hydrolysis are typically around pH 4.8 at a temperature between 45 and 50° C. with incubations of between 10 and 120 hours. Cellulase loading can vary from around 5 to 35 filter paper units (FPU) of activity per gram of substrate Surfactants like Tween 20, 80, polyoxyethylene glycol or Tween 81 may also be used during enzyme hydrolysis to improve cellulose conversion. Additionally, combinations or mixtures of available cellulases and other enzymes may also lead to increased saccharification.

Aside from enzymatic hydrolysis, cellulose may also be hydrolyzed with weak acids or hydrochloric acid (Lee et al., 1999).

C. Fermentation

Once fermentable sugars have been produced from the lignocellulosic biomass, those sugars may be used to produce ethanol via fermentation. Fermentation processes for producing ethanol from lignocellulosic biomass are extensively reviewed in Olsson and Hahn-Hagerdal (1996). Briefly, for maximum efficiencies, both pentose sugars from the hemicellulose fraction of the lignocellulosic material (e.g., xylose) and hexose sugars from the cellulose fraction (e.g., glucose) should be utilized. *Saccharomyces cerevisiae* are widely used for fermentation of hexose sugars. Pentose sugars, released from the hemicellulose portion of the biomass, may be fermented using genetically engineered bacteria, including *Escherichia coli* (U.S. Pat. No. 5,000,000) or *Zymomonas mobilis* (Zhang et al., 1995). Fermentation with yeast strains is typically optimal around temperatures of 30 to 37° C.

D. Simultaneous Saccharification and Fermentation (SSF)

Cellulase activity is inhibited by its end products, cellobiose and glucose. Consequently, as saccharification proceeds, the build up of those end products increasingly inhibits continued hydrolysis of the cellulose substrate. Thus, the fermentation of sugars as they are produced in the saccharification process leads to improved efficiencies for cellulose utilization (e.g., U.S. Pat. No. 3,990,944). This process is known as simultaneous saccharification and fermentation (SSF), and is an alternative to the above described separate saccharification and fermentation steps. In addition to increased cellulose utilization, SSF also eliminates the need for a separate vessel and processing step. The optimal temperature for SSF is around 38° C., which is a compromise between the optimal temperatures of cellulose hydrolysis and sugar fermentation. SSF reactions can proceed up to 5 to 7 days.

E. Distillation

The final step for production of ethanol is distillation. The fermentation or SSF product is distilled using conventional methods producing ethanol, for instance 95% ethanol.

II. PLANT TRANSFORMATION CONSTRUCTS

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al., (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. The PAL2 promoter may in particular be useful with the invention (U.S. Pat. Appl. Pub. 2004/0049802, the entire disclosure of which is specifically incorporated herein by reference). In one embodiment of the invention, the native promoter of a lignin biosynthesis coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that lignin biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a lignin biosynthesis coding sequence is used. Alternatively, a heterologous 3' end may enhance the expression of sense or antisense lignin biosynthesis coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable" markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR—S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. ANTISENSE AND RNAI CONSTRUCTS

Antisense and RNAi treatments represent one way of altering lignin biosynthesis activity in accordance with the invention (e.g., by down regulation of NST transcription factor). In particular, constructs comprising a lignin biosynthesis coding sequence, including fragments thereof, in antisense orientation, or combinations of sense and antisense orientation, may be used to decrease or effectively eliminate the expression of a lignin biosynthesis gene in a plant and obtain an improvement in lignin profile as is described herein. Accordingly, this may be used to "knock-out" the function of a lignin biosynthesis coding sequence or homologous sequences thereof.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 30, 50, 75 or 100 or more contiguous nucleic acids of the nucleic acid sequence of a lignin biosynthesis gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. Methods for selection and design of sequences that generate RNAi are well known in the art (e.g., Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

IV. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species, including biofuel crop species, may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Similarly, *Agrobacterium* mediated transformation has also proven to be effective in switchgrass. Somleva et al., (2002) describe the creation of approximately 600 transgenic switchgrass plants carrying a bar gene and a uidA gene (beta-glucuronidase) under control of a maize ubiquitin promoter and rice actin promoter respectively. Both genes were expressed in the primary transformants and could be inherited and expressed in subsequent generations. Addition of 50 to 200 M acetosyringone to the inoculation medium increased the frequency of transgenic switchgrass plants recovered.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martine-11, 1993), tomato (VanEck et al., 1995), and legumes in general (U.S. Pat. No. 5,563,055, specifically incorporated herein by reference in its entirety).

Richards et al., (2001) describe the creation of transgenic switchgrass plants using particle bombardment. Callus was bombarded with a plasmid carrying a sgfp (green fluorescent protein) gene and a bar (bialaphos and Basta tolerance) gene under control of a rice actin promoter and maize ubiquitin promoter respectively. Plants regenerated from bombarded callus were Basta tolerant and expressed GFP. These primary transformants were then crossed with non-transgenic control plants, and Basta tolerance was observed in progeny plants, demonstrating inheritance of the bar gene.

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. BACTOAGAR, GELRITE, and GELGRO are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

V. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318).

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins m-2 s-1 of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and 14C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VI. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected lignin biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. DEFINITIONS

Biofuel crop species: A plant that may be used to provide biomass for production of lignocellulosic-derived ethanol. Examples of such plants include switchgrass (*Panicum virgatum*), giant reed (*Arundo donax*), reed canarygrass (*Phalaris arundinacea*), Miscanthus×giganteus, Miscanthus sp., sericea lespedeza (*Lespedeza cuneata*), corn, sugarcane, sorghum, millet, ryegrass (*Lolium multiflorum, Lolium* sp.), timothy, Kochia (*Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, fonio (*Digitaria* sp.), and poplar, among others.

Expression: The combination of intracellular processes, including transcription and translation undergone by a coding DNA molecule such as a structural gene to produce a polypeptide.

Forage crops: Crops including grasses and legumes used as fodder or silage for livestock production.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

R0 transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation and Characterization of *M. truncatula* NST1 Mutants

To identify mutants with defects in secondary cell wall formation, a R1 population of tobacco Tnt1 retrotransposon insertion-mutagenized *M. truncatula* (see, e.g., Tadege et al., 2005; Tadege et al., 2008) was screened by UV microscopy of cross-sections of the 6th internodes of stems. Plants were grown in MetroMix 350 soil mix at 24° C. day/20° C. night temperature, 16 h day/8 h night photoperiod, 70-80% relative humidity, and 150 µmol/m$^2$/s light intensity. Sixth internodes of each plant were harvested when the plants had reached around eight internodes, and were stored at −80° C. Cross section of *Medicago* stems (100 µm) from the sixth internode from the top were cut with a Leica RM 2255 microtome. The micrographs were taken under a Nikon Micophot-FX system with a Nikon DXM 1200 color camera. Four nst1 alleles were identified from screening of a segregating population of approximately 9,000 independent R1 lines.

Approximately 3,400 independent R1 lines (around 10,000 plants) were analyzed and several lines with significantly altered extents and/or patterns of lignin autofluorescence were observed. Of these lines, one with a specific defect in the deposition of lignin in interfascicular fibers was identified as being of particular interest. To better characterize developmental patterns of lignification in this mutant (line NF3056), lignin autofluorescence in cross-sections from the $2^{nd}$-$5^{th}$ internodes (from top to bottom) was compared between NF3056 and wild-type R108 *M. truncatula*. In the wild-type plant, lignin starts to accumulate in vascular tissues at an early stage, and is most intensely located in secondary walls of vascular tissues, pith rays and fibers at late stages. Compared with the wild-type plant, NF3056 demonstrated no difference in the location or intensity of lignin autofluorescence at the early stage, but there was clearly less lignin in the $3^{rd}$ internode and below, and the lignin was only deposited in vascular cells, in contrast to the strong lignification in the interfascicular region in the wild-type. The level of lignin autofluorescence in vascular elements appeared similar in the wild-type and mutant lines. Maule staining revealed intense S lignin in secondary walls of vascular tissues, fibers and pith rays in wild-type plants, but very low amounts of S lignin were observed, in vascular cells only, in NF3056.

To identify the gene which is responsible for the loss of interfascicular lignification phenotype, Affymetrix® microarray analysis was performed with RNA isolated from lignifying stem internodes of NF3056. Because *Medicago* Tnt1 retrotransposon lines contain from 20-50 insertions (Tadege et al., 2008), progeny from the same parent plant segregating with wild-type lignification phenotype were used as the controls. Total RNA samples from triplicate biological replicates of the mutants and controls were subjected to Affymetrix® microarray analysis. One hundred and fifty two probe sets were down-regulated in the mutant line by at least 2-fold (Table 1). To identify the gene with the Tnt1 retrotransposon insertion, PCR was performed with a Tnt1 primer and primers designed from the probe set sequences; this was done sequentially in order of the extent of down-regulation of the 152 probe-sets. PCR amplification using primers complementary to the three most down-regulated genes in Table 1, each of which is annotated as encoding a gene involved in cell wall biosynthesis, did not lead to amplification of a PCR product, while the fourth candidate (Mtr.33913.1.S1_at, expression level decreased by 22 fold) was confirmed to contain a Tnt1 retrotranspon insert. The probe set Mtr.33913.1.S1_at is annotated as representing a NAM (no apical meristem)-like protein.

TABLE 1

Microarray analysis of NST regulated genes

| Probesets | Annotation | NF2911 Ratio(M/W) | NF3056 Raio(M/W) |
|---|---|---|---|
| Mtr.37356.1.S1_at | CYP71B34 | CYP71B34 (cytochrome P450, family 71, subfamily B e−177 | 12.43 | 3.39 |
| Mtr.37358.1.S1_s_at | CYP71B13 | CYP71B13 (cytochrome P450, family 71, subfamily B 4e−90 | 12.11 | 3.23 |
| Mtr.38768.1.S1_at | oxidoreductase, 2OG-Fe(II) oxygenase family protein e−111 | 7.33 | 3.27 |
| Mtr.25156.1.S1_s_at | CYP71B9 cytochrome P450 | 4.93 | 3.05 |
| Mtr.11256.1.S1_at | predicted protein | 4.65 | 2.63 |
| Mtr.51818.1.S1_at | predicted protein | 4.59 | 2.73 |
| Mtr.25156.1.S1_at | CYP71B9 cytochrome P450 | 4.51 | 2.95 |
| Mtr.42500.1.S1_at | Gibberellin 2-oxidase | 4.51 | 2.72 |
| Mtr.27695.1.S1_at | glycine-rich protein | 3.75 | 2.35 |

TABLE 1-continued

Microarray analysis of NST regulated genes

| Probesets | Annotation | NF2911 Ratio(M/W) | NF3056 Raio(M/W) |
|---|---|---|---|
| Mtr.45270.1.S1_at | predicted protein | 3.75 | 2.15 |
| Mtr.43098.1.S1_at | Lutein-deficient 1 (LUT1) required for lutein biosynthesis, member of the xanthophyll class of carotenoids. Involved in epsilon ring hydroxylation | 3.58 | 2.17 |
| Mtr.5939.1.S1_s_at | Lutein-deficient 1 (LUT1) required for lutein biosynthesis, member of the xanthophyll class of carotenoids. Involved in epsilon ring hydroxylation | 3.54 | 2.14 |
| Mtr.42053.1.S1_at | lysine and histidine specific transporter, putative 7e-14 | 3.12 | 3.39 |
| Mtr.18939.1.S1_at | lysine and histidine specific transporter, putative 0.0 | 2.98 | 2.07 |
| Mtr.42989.1.S1_at | ATOSM34 | ATOSM34 (OSMOTIN 34) | 2.98 | 2.01 |
| Mtr.14159.1.S1_at | Zn-finger, Dof type DNA binding | 2.49 | 2.16 |
| Msa.1456.1.S1_at | CYP71B14 | CYP71B14 (cytochrome P450, family 71, subfamily B | 2.34 | 1.13 |
| Mtr.34412.1.S1_at | ATMYB103 (MYB DOMAIN PROTEIN 103); DNA binding/transcription factor | 2.04 | 2.16 |
| Mtr.35802.1.S1_at | U-box domain-containing protein | 2.04 | 2.14 |
| Mtr.42553.1.S1_s_at | CYP84A1, FAH1 | FAH1 (FERULATE-5-HYDROXYLASE 1); F5H | 0.02 | 0.04 |
| Mtr.20710.1.S1_at | Cytochrome P450 CYP84A1, FAH1 | FAH1 (FERULATE-5-HYDROXYLASE 1); ferulate 5-hydroxylase | 0.03 | 0.05 |
| Mtr.39454.1.S1_at | ATFXG1 | ATFXG1 (ALPHA-FUCOSIDASE 1); able to release the t-fucosyl residue from the side chain of xyloglucan | 0.03 | 0.09 |
| Mtr.33913.1.S1_at | NAM | 0.04 | 0.05 |
| Mtr.25494.1.S1_at | ATGOLS1 | ATGOLS1 (*ARABIDOPSIS THALIANA* GALACTINOL SYNTHASE 1); transferase, transferring hexosyl groups | 0.07 | 0.39 |
| Mtr.1416.1.S1_s_at | predicted protein | 0.07 | 0.18 |
| Mtr.42985.1.S1_at | germin-like protein, putative 1e-91 | 0.07 | 0.16 |
| Msa.1740.1.S1_at | FAH1 (FERULATE-5-HYDROXYLASE 1); ferulate 5-hydroxylase | 0.08 | 0.35 |
| Mtr.23049.1.S1_at | transferase, transferring glycosyl groups | 0.08 | 0.13 |
| Mtr.10628.1.S1_at | CYP84A1, FAH1 | FAH1 (FERULATE-5-HYDROXYLASE 1); | 0.09 | 0.31 |
| Mtr.1416.1.S1_at | predicted protein | 0.10 | 0.38 |
| Mtr.1415.1.S1_s_at | transferase, transferring glycosyl groups 0.005 | 0.10 | 0.33 |
| Mtr.42942.1.S1_at | protein kinase, putative | 0.15 | 0.20 |
| Mtr.25118.1.S1_at | SAW2, BLH4 | BLH4 (SAWTOOTH 2); DNA binding transcription factor | 0.17 | 0.37 |
| Mtr.49754.1.S1_at | RIC4 (ROP-INTERACTIVE CRIB MOTIF-CONTAINING protein 4 | 0.17 | 0.16 |
| Mtr.39737.1.S1_at | LAC17 | LAC17 (laccase 17); copper ion binding | 0.18 | 0.02 |
| Mtr.25118.1.S1_s_at | SAW2, BLH4 | BLH4 (SAWTOOTH 2); DNA binding transcription factor | 0.18 | 0.38 |
| Mtr.32593.1.S1_at | leucine-rich repeat family protein extensin like root hair morphology cell wall | 0.18 | 0.09 |
| Mtr.13653.1.S1_at | LAC17 (laccase 17); copper ion binding | 0.19 | 0.04 |
| Mtr.28188.1.S1_at | S-adenosyl-L-methionine: carboxyl methyltransferase | 0.19 | 0.45 |
| Mtr.30687.1.S1_at | similar to unknown protein | 0.19 | 0.16 |
| Mtr.12507.1.S1_at | ATSBT5.2; subtilase | 0.19 | 0.14 |
| Mtr.762.1.S1_at | 2-oxoglutarate-dependent dioxygenase, putative | 0.20 | 0.16 |
| Mtr.15958.1.S1_s_at | Zn-finger, CCHC type; Peptidase aspartic; Peptidase S8 and S53, subtilisin, kexin, sedolisin | 0.20 | 0.38 |
| Mtr.39011.1.S1_at | GLP1 | GLP1 (GERMIN-LIKE PROTEIN 1); manganese ion binding | 0.20 | 0.12 |
| Mtr.29418.1.S1_at | unknown protein | 0.20 | 0.22 |
| Mtr.49899.1.S1_s_at | EXPB2, ATHEXP BETA 1.4, ATEXPB2 | ATEXPB2 (*ARABIDOPSIS THALIANA* EXPANSIN B2 | 0.21 | 0.38 |
| Mtr.28665.1.S1_at | unknown protein | 0.22 | 0.18 |
| Mtr.23786.1.S1_at | Expressed protein | 0.25 | 0.10 |
| Mtr.2885.1.S1_at | methyladenine glycosylase family protein | 0.25 | 0.34 |
| Mtr.36197.1.S1_at | similar to unknown protein | 0.26 | 0.48 |
| Mtr.46558.1.S1_at | unknown protein | 0.27 | 0.07 |
| Mtr.39376.1.S1_at | ANAC073 | ANAC073 (*Arabidopsis* NAC domain containing protein 73 9e-29 SND2 | 0.27 | 0.23 |
| Mtr.51876.1.S1_at | peroxidase 64 (PER64) (P64) (PRXR4) e-138 | 0.28 | 0.27 |
| Mtr.43288.1.S1_at | IRX12, LAC4 | IRX12/LAC4 (laccase 4); copper ion binding, might be involved in cell wall biosynthesis. Mutants have a mild irregular xylem phenotype 0 | 0.28 | 0.23 |
| Mtr.33788.1.S1_at | IRX7, FRA8 | FRA8 (FRAGILE FIBER8); transferase Expect = 2e-04 kind of low | 0.28 | 0.41 |
| Mtr.4733.1.S1_s_at | peroxidase 64 (PER64) (P64) (PRXR4) 4e-27 tightly-bound wall proteins from cell wall proteome | 0.28 | 0.20 |
| Mtr.33463.1.S1_s_at | molybdenum cofactor sulfurase family protein | 0.29 | 0.33 |
| Mtr.4733.1.S1_at | peroxidase 64 (PER64) (P64) (PRXR4) 4e-27 tightly-bound wall proteins from cell wall proteome | 0.29 | 0.19 |
| Mtr.5547.1.S1_s_at | ANAC073 | ANAC073 (*Arabidopsis* NAC domain containing protein 73 9e-29 SND2 | 0.29 | 0.24 |
| Mtr.46721.1.S1_at | CYP72A13 | CYP72A13 (cytochrome P450, family 72, subfamily A number 72 | 0.29 | 0.37 |
| Mtr.38153.1.S1_at | molybdenum cofactor sulfurase family protein | 0.30 | 0.36 |
| Mtr.9913.1.S1_s_at | proton-dependent oligopeptide transport (POT) family protein e-101 | 0.31 | 0.49 |
| Mtr.46962.1.S1_at | dehydration-responsive family protein | 0.31 | 0.41 |
| Mtr.41085.1.S1_at | similar to unknown protein | 0.31 | 0.36 |
| Mtr.16615.1.S1_at | ADT3, PD1 | PD1 (PREPHENATE DEHYDRATASE 1); arogenate dehydratase/ prephenate dehydratase involved in phenylalanine biosynthesis | 0.31 | 0.42 |
| Mtr.14580.1.S1_at | zinc finger (C3HC4-type RING finger) family protein | 0.32 | 0.22 |
| Mtr.10332.1.S1_at | PR3, PR-3, CHI-B, B-CHI, ATHCHIB | ATHCHIB (BASIC CHITINASE); chitinase | chr3: 3962389-3963971 REVERSE e-110 | 0.33 | 0.39 |
| Mtr.9283.1.S1_at | similar to unknown protein, contains Interpro domain Protein of unknown function DUF231 0.0 | 0.33 | 0.30 |
| Mtr.13425.1.S1_s_at | IQD21 (IQ-DOMAIN 21, IQ-domain 21); calmodulin binding; similar to IQD5 (IQ-domain 5), calmodulin binding | 0.34 | 0.30 |
| Mtr.44275.1.S1_s_at | IQD21 | IQD21 (IQ-DOMAIN 21, IQ-domain 21); calmodulin binding 1e-22 | 0.35 | 0.31 |

TABLE 1-continued

Microarray analysis of NST regulated genes

| Probesets | Annotation | NF2911 Ratio(M/W) | NF3056 Raio(M/W) |
|---|---|---|---|
| Mtr.12632.1.S1_at | CYP81D3 cytochrome P450 | 0.35 | 0.35 |
| Mtr.20062.1.S1_at | CLE12 \| CLE12 (CLAVATA3/ESR-RELATED 12); receptor binding | 0.35 | 0.29 |
| Mtr.41429.1.S1_at | GATL1, PARVUS, GLZ1 \| GATL1/GLZ1/PARVUS GALACTURONOSYLTRANSFERASE-LIKE 1); polygalacturonate 4-alpha-galacturonosyltransferase/transferase e−169 | 0.35 | 0.35 |
| Mtr.50224.1.S1_s_at | CESA7, ATCESA7, MUR10, IRX3 \| IRX3 (IRREGULAR XYLEM 3 Cellulose synthase | 0.36 | 0.30 |
| Mtr.17860.1.S1_at | Protein of unknown function DUF231 | 0.36 | 0.19 |
| Mtr.26304.1.S1_at | peptidoglycan-binding LysM domain-containing protein | 0.37 | 0.44 |
| Mtr.40320.1.S1_at | IRX7, FRA8 \| FRA8 (FRAGILE FIBER8); transferase is involved in secondary cell wall biosynthesis expressed specifically in developing vessels and fiber cells, and FRA8 is targeted to Golgi. Mutants have irregular xylem formation, reduced cellulose levels a | 0.38 | 0.42 |
| Mtr.41311.1.S1_at | GAUT12, LGT6, IRX8 \| GAUT12/IRX8/LGT6 GALACTURONOSYLTRANSFERASE 12; polygalacturonate 4-alpha-galacturonosyltransferase e−163 | 0.38 | 0.31 |
| Mtr.30695.1.S1_at | GAUT12, LGT6, IRX8 \| GAUT12/IRX8/LGT6 GALACTURONOSYLTRANSFERASE 12; polygalacturonate 4-alpha-galacturonosyltransferase | 0.39 | 0.31 |
| Mtr.49172.1.S1_at | hypothetical protein | 0.39 | 0.37 |
| Mtr.47815.1.S1_at | AGD8 \| AGD8 (ARF-GAP DOMAIN 8); DNA binding | 0.39 | 0.48 |
| Mtr.35578.1.S1_at | ATMAP70-2, F5A9.19, F5A9_19, MICROTUBULE-ASSOCIATED PROTEINS 70-2 | 0.39 | 0.35 |
| Mtr.9169.1.S1_at | nucleic acid binding/pancreatic ribonuclease e−128 | 0.40 | 0.32 |
| Mtr.10312.1.S1_at | COL4/IRX6 phytochelatin synthetase. Involved in secondary cell wall biosynthesis. Mutants make smaller plants with reduced levels of cellulose and cell wall sugars | 0.40 | 0.27 |
| Mtr.22376.1.S1_at | Protein of unknown function DUF246 | 0.40 | 0.48 |
| Mtr.46961.1.S1_at | dehydration-responsive family protein | 0.40 | 0.45 |
| Mtr.7397.1.S1_at | predicted protein | 0.40 | 0.48 |
| Mtr.44524.1.S1_at | ARPC2B \| ARPC2B (actin-related protein C2B), structural molecule; similar to ARPC2A/DIS2 (DISTORTED TRICHOMES 2), | 0.41 | 0.35 |
| Mtr.33547.1.S1_at | CESA8, IRX1, ATCESA8, LEW2 \| CESA8 (CELLULOSE SYNTHASE) | 0.42 | 0.34 |
| Mtr.5242.1.S1_at | CESA8, IRX1, ATCESA8, LEW2 \| CESA8 (CELLULOSE SYNTHASE 8); 4e−65 | 0.42 | 0.37 |
| Mtr.39566.1.S1_at | kinesin light chain-related | 0.43 | 0.41 |
| Mtr.39117.1.S1_at | kinesin light chain-related | 0.43 | 0.39 |
| Mtr.13202.1.S1_at | CESA8, IRX1, ATCESA8, LEW2 \| CESA8 (CELLULOSE SYNTHASE 8); | 0.43 | 0.36 |
| Mtr.11636.1.S1_at | Dof-type zinc finger domain-containing protein | 0.43 | 0.35 |
| Mtr.48097.1.S1_at | similar to unknown protein | 0.43 | 0.37 |
| Mtr.24892.1.S1_at | ATBXL2, BXL2 \| BXL2 (BETA-XYLOSIDASE 2); hydrolase involved in secondary wall hemicellulose metablism | 0.43 | 0.28 |
| Mtr.11390.1.S1_at | Encodes ESK1 (Eskimo1). A member of a large gene family of DUF231 domain proteins whose members encode a total of 45 proteins of unknown function. ESK1 functions as a negative regulator of cold acclimation. Mutations in the ESK1 gene provides strong | 0.43 | 0.41 |
| Mtr.24619.1.S1_at | Expressed protein | 0.44 | 0.30 |
| Mtr.13814.1.S1_at | glycoside hydrolase family 28 protein, polygalacturonase (pectinase) family protein | 0.45 | 0.50 |
| Mtr.41481.1.S1_at | transporter-related | 0.45 | 0.48 |
| Mtr.32451.1.S1_s_at | ATBXL2, BXL2 \| BXL2 (BETA-XYLOSIDASE 2); hydrolase | 0.45 | 0.28 |
| Mtr.9427.1.S1_at | F-box family protein e−131 | 0.45 | 0.35 |
| Mtr.50411.1.S1_at | methyladenine glycosylase family protein | 0.46 | 0.35 |
| Mtr.38262.1.S1_at | IRX14 \| IRX14 (IRREGULAR XYLEM 14); transferase glycosyl transferase that contributes to xylan biosynthesis | 0.46 | 0.37 |
| Mtr.18524.1.S1_at | KATC, ATK3 \| ATK3 (ARABIDOPSIS THALIANA KINESIN 3); microtubule motor | 0.46 | 0.36 |
| Mtr.10615.1.S1_at | ATCESA7, CELLULOSE SYNTHASE CATALYTIC SUBUNIT 7, CESA7, IRREGULAR XYLEM 3, IRX3 | 0.47 | 0.39 |
| Mtr.42734.1.S1_at | LAC12 \| LAC12 (laccase 12); copper ion binding | 0.47 | 0.19 |
| Mtr.40627.1.S1_at | glycosyl hydrolase family 3 protein | 0.47 | 0.46 |
| Mtr.24893.1.S1_at | ATBXL2, BXL2 \| BXL2 (BETA-XYLOSIDASE 2); hydrolase involved in secondary wall hemicellulose metablism | 0.47 | 0.30 |
| Mtr.8830.1.S1_at | aspartyl protease family protein | 0.48 | 0.49 |
| Mtr.11798.1.S1_at | CESA8, IRX1, ATCESA8, LEW2 \| CESA8 (CELLULOSE SYNTHASE 8) Cellulose synthase | 0.48 | 0.41 |
| Mtr.4126.1.S1_at | LAC17 \| LAC17 (laccase 17); copper ion binding | 0.48 | 0.28 |
| Mtr.17362.1.S1_at | FLA12 (fasciclin-like arabinogalactan-protein) | 0.49 | 0.20 |
| Mtr.5557.1.S1_at | glycosyl hydrolase family 3 protein 1e−68 same family as bxl2 and 3 | 0.49 | 0.47 |

Using the Mtr.33913.1.S1_at probe sequence, a cDNA BLAST search was performed against the M. truncatula genome from Dana Farber Cancer Institute (DFCI), available from the DFCI web site at compbio.dfci.harvard.edu/tgi/cgi-bin/tgi/gimain.pl?gudb=Medicago). The first hit with the lowest e-value was TC141793, which contains a 1113 bp cDNA sequence including the entire Mtr.33913.1.S1_at probe sequence. Using the TC141793 sequence, a nucleotide BLAST search was then performed against the NCBI database, and the first hit was with a sequence encoding Arabidopsis NST1 (AtNST1), a recently discovered NAC transcription factor responsible for secondary wall thickening (Zhong et al., 2007). Because TC141793 does not contain the full-length cDNA, 3'-RACE was performed to complete the cDNA sequence. Because NF3056 phenocopies the Arabidopsis nst1 nst3 double mutant, and TC141793 shares sequence similarity with Arabidopsis nst1, the full length sequence was named MtNST1, and the NF3056 mutant designated as NST1-1.

Figure 1A:
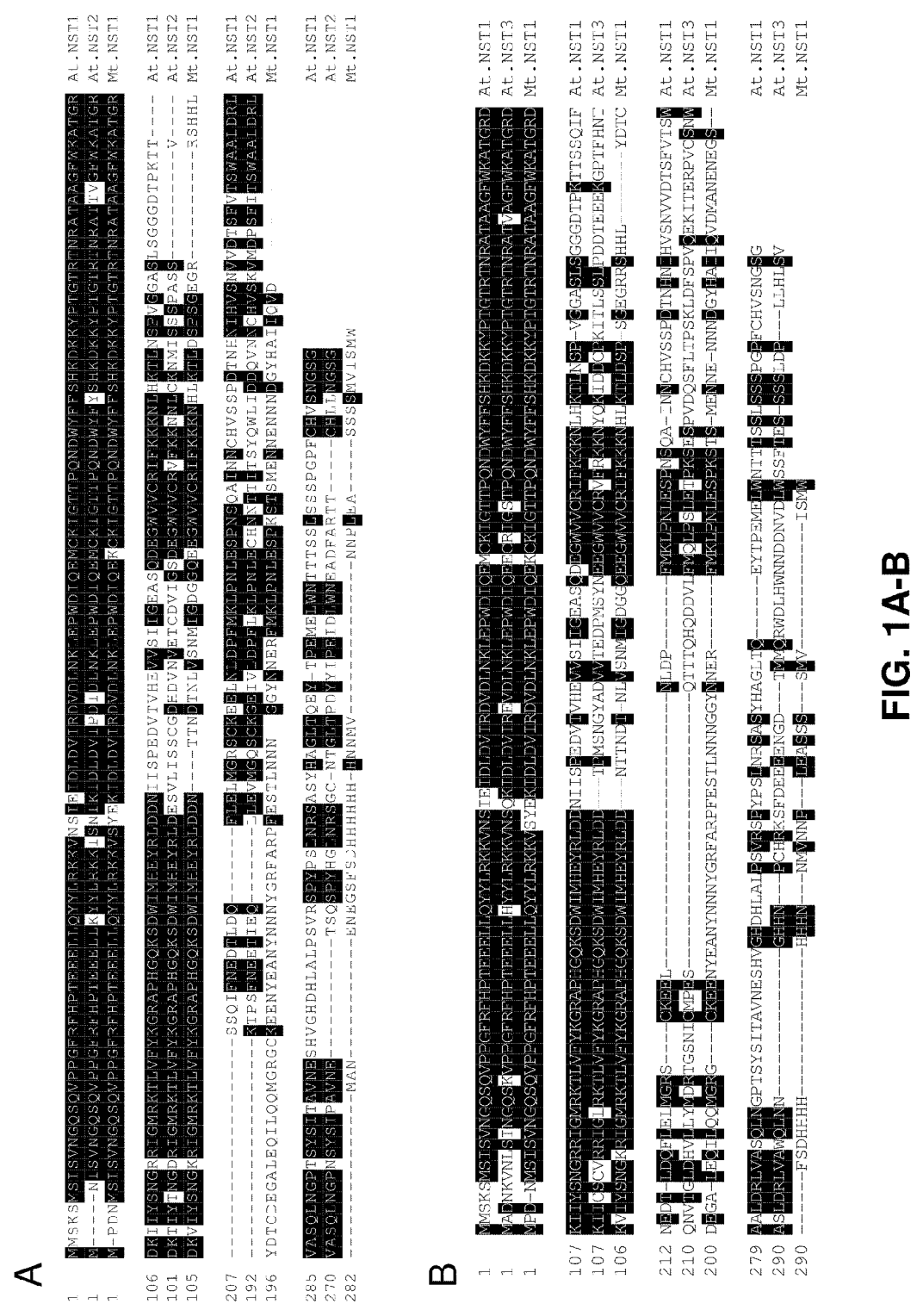

Protein alignment was performed using the translated sequences from TC141793 and *Arabidopsis* NST1, NST2 and NST3. Because the *Arabidopsis* nst1 nst2 and nst1 nst3 double mutants have different phenotypes, MtNST1 was aligned separately with AtNST1 and NST3, and with AtNST1 and NST2 (FIG. 1A-B). MtNST1 shares significant sequence similarity with all AtNST proteins at the conserved N-terminal NAC domain. The level of conservation is comparable to that between AtNST proteins. However, the C-terminal domain of MtNST1 is quite distinct, indicating that MtNST1 might have different functional characteristics. The overall sequence similarity between MtNST1 and AtNST proteins is only around 50% even though the NAC domain is highly conserved.

To further confirm that the loss of lignification phenotype was indeed the result of insertional mutagenesis of MtNST1, PCR amplification of genomic DNA was performed with additional Tnt1 lines exhibiting a similar phenotype, and three lines lacking lignin autofluorescence in the interfascicular region, NF2911, NF4041 and NF3687, were confirmed to have a Tnt1 insertion in the same gene. Tnt1 flanking sequence analyses indicated that Tnt1 was inserted in the NST1 gene in the first exon at position 43 bp (NST1-1, NF3056), 170 bp (NST1-2, NF2911) and in the second exon at position 586 bp (NST1-3, NF4041), and 437 bp (NST1-4, NF3687) (FIG. 2A). RT-PCR analysis confirmed that no MtNST1 transcript was present in any of the four mutant lines (FIG. 2B).

Example 2

Additional Phenotypes of *M. truncatula* NST1 Mutants

At first sight, the overall growth phenotypes of the four independent nst1 mutant lines appeared similar to those of wild-type plants, although the branches were less able to support themselves against gravity, presumably due to the defect in secondary wall formation. Vegetative growth was not strongly affected in the Mt-NST1 mutant lines, but stem length was reduced by around 25% and leaf area increased by around 14% (Table 2). The reduction in stem length was mainly the result of reduction of internode length in the last 3 internodes below the flowering node. Flowering time and stem diameter were not affected in the mutant lines (Table 2).

TABLE 2

Characterization of control (Wt 1-3) and MtNST (Mtr-nst1/1-3) mutant lines.

| Line | Stem height (cm) | Flowering Node | Internodes length media (cm) | Leaf area (mm$^2$) | Stem diameter (mm) | Photosynthetic rate ($\mu$molCO$_2 \cdot$ m$^{-2} \cdot$ s$^{-1}$) | Transpiration rate ($\mu$molH$_2$O $\cdot$ m$^{-2} \cdot$ s$^{-1}$) | Stomata aperture |
|---|---|---|---|---|---|---|---|---|
| Wt1 | 70.4 ± 0.5 | 11.5 ± 0.6 | 5.9 ± 0.5 | 5.0 ± 0.2 | 1.6 ± 0.2 | 13.1 ± 0.2 | 4.5 ± 0.1 | 1.5 ± 0.3 |
| Mtr-nst1-1 | 60.8 ± 0.6 | 11 ± 0.3 | 5.1 ± 0.2 | 6.4 ± 0.3 | 1.6 ± 0.1 | 14.2 ± 0.3 | 3.9 ± 0.2 | 3.6 ± 0.3 |
| Wt2 | 67.7 ± 0.7 | 10.8 ± 0.6 | 5.7 ± 0.5 | 9.1 ± 0.5 | 2 ± 0.2 | 14.2 ± 0.1 | 4.1 ± 0.2 | 1.7 ± 0.2 |
| Mtr-nst1-2 | 65 ± 0.6 | 12 ± 0.8 | 5.4 ± 0.4 | 11 ± 0.8 | 1.9 ± 0.3 | 15.8 ± 0.2 | 3.5 ± 0.2 | 4.6 ± 0.3 |
| Wt3 | 70.3 ± 0.4 | 11.5 ± 0.6 | 5.9 ± 0.3 | 6.2 ± 0.4 | 1.6 ± 0.1 | 14.2 ± 0.3 | 4.3 ± 0.1 | 1.8 ± 0.2 |
| Mtr-nst1-3 | 61.5 ± 0.4 | 11 ± 0.7 | 5.1 ± 0.3 | 7.3 ± 0.8 | 1.8 ± 0.2 | 15.3 ± 0.1 | 3.6 ± 0.1 | 5.2 ± 0.3 |
| Average* | | | | | | | | |
| Wt | 69.5 ± 0.3 | 11.2 ± 0.5 | 5.8 ± 0.2 | 6.9 ± 0.6 | 1.73 ± 0.1 | 13.8 ± 0.2 | 4.3 ± 0.1 | 1.6 ± 0.2 |
| Mtr-nst1/1-3 | 62.4 ± 0.4 | 11.3 ± 0.6 | 5.2 ± 0.3 | 8.1 ± 0.7 | 1.76 ± 0.2 | 15.1 ± 0.2 | 3.6 ± 0.2 | 4.46 ± 0.3 |

Results in Table 2 are the means of 6 stems per line in the case of phenotypic features.
Photosynthetic and transpiration rate are the means of 6 values (3 replicates taken on two different days) ± SE. The stomata aperture data is the mean of 75 stomata guard cell lengths distributed in 3 different areas of the film strips ± SE.
*is the average of the single data for Wt 1-3 and Mtr-nst1/1-3.

Photosynthetic rate increased by 10% but transpiration rate was reduced by 12% in MtNST1 mutants lines compared to wild-type (Table 2). Examination of leaf epidermal cells revealed a significant loss of fluorescence signal (originating from wall-bound ferulic acid (Jones et al., 2005)) in stomatal guard cells of mutant leaves compared to wild-type. This was observed in all four independent NST1 alleles. Furthermore, after a light induction period, the guard cells of the NST1 mutant exhibited a striking reduction in stomatal aperture of around 80% compared to controls (Table 2).

*Arabidopsis* NST1 and NST2 together regulate secondary wall thickening in the anther endothecium, and nst1 nst2 double mutants show a defect in anther dehiscence (Mitsuda et al., 2005, 2007). MtNST1 flowers likewise have indehiscent anthers, while the pollen grains are normally released from wild-type anthers. To examine pollen viability in the NST1 flowers, Alexander's staining method was used (Alexander, 1969). Light microscopy showed that the pollen grains from MtNST1-1 take up the stain and are therefore viable; they also exhibit normal shape and size. *M. truncatula* is a self pollinating species; as a result of the impairment of anther dehiscence, mature plants of the NST1-1 line fail to develop seed pods.

Example 3

Cell Wall Composition of Mtnst1 Mutants

The total lignin content of stem internodes 5-8, as determined by the acetyl bromide method (Fukushima and Hatfield, 2004) using ~15 mg extractive-free material (Hatfield et al., 1999). The same molar extinction coefficient of 17.2 (as determined for lignin from wild-type alfalfa) was used for samples for all the transgenic lines. Thioacidolysis methods were used for the determination of lignin composition. Thioacidolysis was performed using ~20 mg of extractive-free samples reacted with 3 ml of 0.2 M BF3 etherate in an 8.75:1 dioxane/ethanethiol mixture. Lignin-derived monomers were identified by gas chromatography mass spectrometry (GC/

MS) and quantified by GC as their trimethylsilyl derivatives, as described previously (Lapierre et al., 1995).

Results of these studies demonstrated that lignin content was reduced by around 50% in the MtNST1 mutant compared with wild-type plants (FIG. 3A). Extractable lignin monomer yields were measured by the thioacidolysis method, and both G and S lignin units were strikingly reduced in the NST1 mutant, with S lignin being virtually undetectable (FIG. 3B; Table 3).

TABLE 3

Analysis of Lignin content

| | G (μmol/g) | S (μmol/g) | Total (μmol/g) | S/G |
|---|---|---|---|---|
| Normal | 426.79 | 70.02 | 496.82 | 0.164 |
| Mutant | 136.20 | 5.49 | 141.68 | 0.040 |

The same cell wall samples used for lignin analysis were analyzed for total sugar content by phenol-sulfuric assay. Total sugar levels were somewhat reduced in NST1 mutants compared with wild-type plants (FIG. 3C). Analysis of monosaccharide composition indicated that glucose, xylose, galactose and arabinose were the major sugar components of the *M. truncatula* cell wall, with galactose levels being significantly higher than in *Arabidopsis* (Zhong et al., 2008) (FIG. 3D). In comparison to wild-type, cell walls from NST1 mutants had slightly decreased levels of glucose and xylose, whereas there was no significant change in galactose or arabinose levels (FIG. 3D). The change in monosaccharide composition is likely due to reduced deposition of cellulose and hemicelluloses in the defective secondary walls of the interfascicular fiber cells.

Example 4

Potential Target Genes for NST1 Action

Because of the existence of multiple Tnt1 insertions in the *Medicago* mutant lines, the initial microarray analysis by which the NST1 gene was identified provides does not provide definitive indication of downstream target genes for NST1 action. A parallel gene expression analysis was therefore performed in an independent allele. Of the 152 probe sets that were down-regulated more than 2-fold in the NST1-1 mutant, 94 were also down-regulated more than 2-fold in the NST1-2 mutant. Eighteen probe sets were also up-regulated more than two-fold in the both mutant lines (Table 1). In view of the lack of overlap in additional Tnt1 flanking sequences recovered from the two lines, these genes represent likely targets for control via NST1.

Of the common down-regulated genes, 12 were involved in lignin biosynthesis, 17 were putatively involved in cellulose or hemicellulose biosynthesis, and 14 were tentatively involved in other aspects of cell wall formation, or with the cytoskeleton (Table 1). The pattern of MtNST1 expression paralleled that of lignin biosynthetic genes during stem development (FIG. 4A).

cDNA samples were used for Quantitative Real-time PCR (qRT-PCR) with technical duplicates. The 10 μl reaction included 2 μl primers (0.5 μM of each primer), 5 μl Power Sybr (Applied Biosystems, Foster City, Calif.), 2 μl 1:20 diluted cDNA from the reverse transcription step, and 1 μl water. qRT-PCR data were analyzed using SDS 2.2.1 software (Applied Biosystems). PCR efficiency was estimated using the LinRegPCR software (Ramakers et al., 2003) and the transcript levels were determined by relative quantification (Pfaffl, 2001) using the *M. truncatula* actin gene as a reference.

Analysis by qRT-PCR confirmed that the expression of multiple genes involved in the biosynthesis of lignin, namely F5H, 4CL, C3H, HCT, CCR, COMT and CCoAOMT was indeed suppressed in the NST1-1 mutant (FIG. 4B). Genes with high sequence similarity to IRX1 and FRA8 were selected to represent genes potentially involved in the cellulose and hemicellulose synthesis pathways, respectively. Because the identities of these two genes in *M. truncatula* have not been experimentally confirmed, three different primer pairs were chosen from each gene for qRT-PCR to ensure accurate determination of gene expression; this confirmed that the expression levels of IRX1 and FRA8 decreased in the NST1 mutants (FIGS. 4C,D). The decreased expression of genes involved in secondary cell wall formation can explain the reduction of lignin and cell wall sugar in the NST1 mutant.

In addition to the inactivated NST1 (NAM) gene, six other probe sets annotated as encoding transcription factors were down-regulated by more than 2-fold in MtNST1-1 and Mtnst 1-2; these comprised two basic helix loop helix (BHLH) genes, two NAC genes, and two zinc finger genes (Table 1).

Example 5

Saccharification Potential of NST1 Mutants

To evaluate the impact of cell wall changes on biomass properties, the mature stems of MtNST1-1 and MtNST1-2 plants were subjected to dilute sulfuric acid pretreatment and enzymatic hydrolysis. Dried stem material at a solid loading of 2% (w/w) was mixed with dilute sulfuric acid (final concentration 1.5% (w/w)) and pretreated in an autoclave at 130° C. for 2 h. After pretreatment, the hydrolysates were separated and collected by filtration from residual biomass and the biomass residues were washed with water. For enzymatic hydrolysis, Celluclast 1.5 L (cellulase from *Trichoderma reesei*) and Novozyme 188 (cellobiase from *Aspergillus niger*) (Sigma Aldrich, St Louis, Mo.) were mixed (equal volumes) and used at a loading of 31.5 FPU per g cell wall residue. Enzymatic saccharification of lignocellulosic material was according to the Laboratory Analytical Procedure of the National Renewable Energy Laboratory (LAP-009). About 0.125 mg cell wall residues were hydrolyzed with a cellulase/cellobiase mix in a total volume of 10 ml by adding appropriate amounts of enzyme mixture and sodium citrate buffer (0.1 M, pH 4.8) for 72 h. Enzyme blanks and Whatman #1 filter paper were digested alongside the samples. Hydrolysis of filter paper was always more than 95%. The total sugar and sugar composition in hydrolysates from chemical pretreatment and enzymatic hydrolysis were determined using the phenol-sufuric acid assay and HPLC. Briefly, determination of carbohydrates was according to the Laboratory Analytical Procedure of the National Renewable Energy Laboratory (LAP-019). Biomass (~300 mg) was first hydrolysed in 72% sulfuric acid at 30° C. then in diluted acid (4%) at 130° C. for 1 h. The solublized sugars were analyzed spectrophotometrically using the phenol-sulfuric acid assay. Monosaccharide compositions were determined by HPLC (Agilent 1200 Series LC System with 1200 Series Refractive Index Detector). An Aminex HPX-87P column was used at 70° C., and the sugars were eluted with Milli-Q filtered water at a flow rate of 0.6 ml/min. Detector temperature was 50° C. Peaks were identified and quantified by comparison to authentic standards.

Compared to the wild type, cell walls from the NST1 mutants released more glucose and less xylose during sulfuric acid pretreatment (FIG. 5A). Without pretreatment, the cellulase mixture could release 64% of the structural sugars from the NST1-1 mutant, significantly high than the wild type (46%). Following acid pretreatment, enzymatic hydrolysis could release 90% of the total sugars (723 mg sugar per gram of cell wall residue) from NST1-1 compared to 67% (572 mg sugar per gram cell wall residue) from wild-type (FIG. 5B). Similar results were obtained with a second allele (NST)-2).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,461,648; U.S. Pat. No. 4,535,060; U.S. Pat. No. 5,000,000; U.S. Pat. No. 5,037,663; U.S. Pat. No. 5,302,523; U.S. Pat. No. 5,322,783; U.S. Pat. No. 5,384,253; U.S. Pat. No. 5,464,765; U.S. Pat. No. 5,508,184; U.S. Pat. No. 5,538,877; U.S. Pat. No. 5,538,880; U.S. Pat. No. 5,545,818; U.S. Pat. No. 5,550,318; U.S. Pat. No. 5,563,055; U.S. Pat. No. 5,591,616; U.S. Pat. No. 5,610,042.
U.S. Pat. Publ 20040049802
Abdullah et al., *Biotechnology*, 4:1087, 1986.
Alexander, *Stain Technol.*, 44: 117-122, 1969.
Bates, *Mol. Biotechnol.*, 2:135-145, 1994.
Battraw et al., *Theor. App. Genet.*, 82:161-168, 1991.
Bevan et al., *Nucleic Acids Research*, 11:369-385, 1983.
Bhattacharjee et al., *J. Plant Bioch. and Biotech.* 6:69-73, 1997.
Bouchez et al., *EMBO J.*, 8:4197-4204, 1989.
Bower et al., *Plant J.*, 2:409-416. 1992.
Buising et al., *Mol Gen Genet*, 243:71-81. 1994.
Callis et al., *Genes Dev.*, 1:1183-1200, 1987.
Casa et al., *Proc. Natl. Acad. Sci. USA*, 90:11212-11216, 1993.
Chandler et al., *Plant Cell*, 1:1175-1183, 1989.
Chen and Dixon, *Nature Biotechnology*, 25: 759-761, 2007.
Christou, et al., *Proc. Natl. Acad. Sci. USA*, 84:3962-3966, 1987.
Chu et al., *Scientia Sinica*, 18:659-668, 1975.
Conkling et al., *Plant Physiol.*, 93:1203-1211, 1990.
De Block et al., *EMBO Journal*, 6:2513-2518, 1987.
De Block et al., *Plant Physiol.*, 91:694-701, 1989.
Dellaporta et al., *Chromosome Structure and Function: Impact of New Concepts, 18th Stadler Genetics Symposium*, 11:263-282, 1988.
Devane et al., *Science*, 258:1946-1949, 1992
D'Halluin et al., *Plant Cell*, 4:1495-1505, 1992.
Dixon, et al., *Rec Adv Phytochem.*, 28:153-178, 1994.
Djerbi et al., *Planta*, 221: 739-746, 2005.
Downward, *BMJ*, 328(7450):1245-1248, 2004.
Duff and Murray, *Bioresource Tech.*, 55:1-33, 1995.
Ebert et al., 84:5745-5749, *Proc. Natl. Acad. Sci. USA*, 1987.
Ellis et al.; *EMBO Journal*, 6:3203-3208, 1987.
Fire et al., *Nature*, 391: 806-11, 1998.
Fraley et al., *Bio/Technology*, 3:629-635, 1985.
Fromm et al., *Nature*, 319:791-793, 1986.
Fukushima and Hatfield, *J. Agric. Food Chem.* 52:3713-3720, 2004.
Gallie et al., *Plant Cell*, 1:301-311, 1989.
Ghosh-Biswas et al., *J. Biotechnol.*, 32:1-10, 1994.
Gong et al., *Adv. Biochem. Engng. Biotech.* 65: 207-241, 1999.
Hagio et al., *Plant Cell Rep.*, 10:260-264, 1991.
Hamilton et al., *Proc. Natl. Acad. Sci. USA*, 93:9975-9979, 1996.
Haseloff et al., *Proc. Natl. Acad. Sci. USA*, 94:2122-2127, 1997.
Hatfield et al., *Crop Science*, 39: 27-37, 1999.
He et al., *Plant Cell Reports*, 14:192-196, 1994.
Hensgens et al., *Plant Mol. Biol.*, 22:1101-1127, 1993.
Hiei et al., *Plant. Mol. Biol.*, 35:205-218, 1997.
Hinchee et al., *Bio/technol.*, 6:915-922, 1988.
Hou et al., *Plant Physiology*, 111:166, 1996.
Hu et al., *Nat. Biotechnol.* 17:808-812, 1999.
Hudspeth et al., *Plant Mol. Biol.*, 12:579-589, 1989.
Ikuta et al., *Bio/Technol.*, 8:241-242, 1990.
Ishidia et al., *Nat. Biotechnol.*, 14:745-750, 1996.
Jones et al., *Planta*, 221: 255-264, 2005.
Kaeppler et al., *Plant Cell Reports*, 9: 415-418, 1990.
Kaeppler et al., *Theor. Appl. Genet.*, 84:560-566, 1992.
Katz et al., *J. Gen. Microbiol.*, 129:2703-2714, 1983.
Keegstra and Walton, *Science*, 311: 1872-1873, 2006.
Kim et al., *Proc Natl Acad. Sci.*, USA 101: 1455-1460, 2004.
Klee et al., *Bio-Technology*, 3:637-642, 1985.
Knittel et al., *Plant Cell Reports*, 14:81-86, 1994.
Lapierre et al., *Res. Chem. Intermed.* 21: 397-412, 1995.
Lawton et al., *Plant Mol. Biol.*, 9:315-324, 1987.
Lazzeri, *Methods Mol. Biol.*, 49:95-106, 1995.
Lee et al., *Adv. Biochem. Eng. Biotech.*, 65: 93-115, 1999
Lee et al., *Korean J. Genet.*, 11:65-72, 1989.
Lehner et al., *Brief Funct Genomic Proteomic*, 3:68-83, 2004.
Lorz et al., *Mol Gen Genet*, 199:178-182, 1985.
Marcotte et al., *Nature*, 335:454, 1988.
Mes-Hartree, et al., *Appl. Microbiol. Biotechnol.*, 29:462-468, 1988.
Mitsuda et al., *Plant Cell*, 17: 2993-3006, 2005.
Mitsuda et al., *Plant Cell* 19:270-280, 2007.
Morjanoff and Gray, *Biotechnol. Bioeng.* 29:733-741, 1987.
Murakami et al., *Mol. Gen. Genet.*, 205:42-50, 1986.
Murashige et al, *Physiol. Plant*, 15:473-497, 1962.
Nagatani et al., *Biotech. Tech.*, 11:471-473, 1997.
Odell et al., *Nature*, 313:810-812, 1985.
Ogawa et al., *Sci. Rep.*, 13:42-48, 1973.
Olsson et al., *Enzyme and Microb. Technol.* 18:312-331, 1996.
Omirulleh et al. *Plant Mol. Biol.*, 21(3):415-428, 1993.
Ow et al., *Science*, 234:856-859, 1986.
PCT App. WO 94/09699
PCT App. WO 95/06128
PCT App. WO 97/41228
PCT App. WO 97/4103
PCT App. WO 92/17598
Pfaffl, *Nucleic Acids Res.*, 29: e45, 2001.
Potrykus et al., *Mol. Gen. Genet.*, 199:183-188, 1985.

Prasher et al.; *Biochem. Biophys. Res. Commun.*, 126:1259-1268, 1985.
Ramakers et al.; *Neurosci Lett.*, 339: 62-66, 2003.
Reddy et al.; *Proc. Nat. Acad. Sci.*, 102:16573-16578, 2005.
Reichel et al.; *Proc. Natl. Acad. Sci*, 93:5888-5893. 1996.
Reynolds, *Nat. Biotechnol.* 22:326-330, 2004.
Rhodes et al.; *Methods Mol. Biol.*, 55:121-131, 1995.
Richards et al.; *Plant Cell Rep.* 20:48-54, 2001.
Ritala et al.; *Plant Mol. Biol.*, 24:317-325, 1994.
Rogers et al.; *Methods Enzymol.*, 153:253-277, 1987.
Sambrook et al.; In: *Molecular Cloning-A Laboratory Manual* (second edition), Cold Spring Harbour Laboratory Press, 1989.
Sheen et al.; *Plant Journal*, 8:777-784, 1995.
Singsit et al., *Transgenic Res.*, 6:169-176, 1997.
Somleva et al., *Crop Science*, 42:2080-2087, 2002.
Stalker et al.; *Science*, 242:419-422, 1988.
Sullivan et al., *Mol. Gen. Genet.*, 215:431-440, 1989.
Sun and Cheng, *Bioresource Technol.* 83:1-11, 2002.
Sutcliffe, *Proc. Natl. Acad. Sci.*, 75:3737-3741, 1978.
Tadege et al., *Trends Plant Sci.*, 10:229-235, 2005.
Tadege et al., *Plant J.*, 54:335-347, 2008.
Thillet et al., *J. Biol. Chem.*, 263:12500-12508, 1988.
Thomas et al., *Plant Sci.* 69:189-198, 1990.
Thompson et al., *Euphytica*, 85:75-80, 1995.
Thompson et al., *The EMBO Journal*, 6:2519-2523, 1987.
Tian, et al., *Plant Cell Rep.*, 16:267-271, 1997.
Tingay et al., *The Plant Journal*, 6:1369-1376. 1997.
Tomes et al., *Plant. Mol. Biol.* 14:261-268, 1990.
Torbet et al., *Crop Science*, 38:226-231, 1998.
Torbet et al., *Plant Cell Reports*, 14:635-640, 1995.
Toriyama et al., *Theor Appl. Genet.*, 73:16, 1986.
Tsukada et al., *Plant Cell Physiol.*, 30:599-604, 1989.
Twell et al., *Plant Physiol.*, 91:1270-1274, 1989.
Uchimiya et al., *Mol. Gen. Genet.*, 204:204, 1986.
Vasil et al., *Plant Physiol.*, 91:1575-1579, 1989.
Walker et al., *Proc. Natl. Acad. Sci. USA*, 84:6624-6628, 1987.
Wang et al., *Molecular and Cellular Biology*, 12:3399-3406, 1992.
Wyman, *Ann. Rev. Energy Environ.* 24:189-226, 1999.
Yamada et al., *Plant Cell Rep.*, 4:85, 1986.
Yang et al., *Proc. Natl. Acad. Sci.*, 87:4144-4148, 1990.
Zhang et al., *Science* 267:240-243, 1995.
Zhong et al., *Plant Cell*, 20:2763-2782, 2008.
Zhong et al., *Planta*, 225:1603-1611, 2007.
Zhou et al., *Plant Cell Reports*, 12:612-616, 1993.
Zukowsky et al., *Proc. Natl. Acad. Sci. USA*, 80:1101-1105, 1983.

What is claimed is:

1. A transgenic switchgrass plant comprising a DNA molecule that is transcribed to an antisense RNA, interfering RNA, or miRNA comprising a unique sequence complementary to a sufficient length of contiguous nucleotides of SEQ ID NO:3 such that the switchgrass plant exhibits reduced lignin content compared to a wild-type plant.

2. The plant of claim 1, wherein the DNA molecule is operably linked to a promoter sequence selected from the group consisting of a developmentally-regulated, organelle-specific, inducible, tissue-specific, constitutive, cell-specific, seed specific, or germination-specific promoter.

3. The plant of claim 1, further defined as an R0 transgenic plant.

4. The plant of claim 1, further defined as a progeny plant of any generation of an R0 transgenic plant, wherein the transgenic plant has inherited the selected DNA from the R0 transgenic plant.

5. The plant of claim 1, further comprising a second DNA sequence that down regulates lignin biosynthesis.

6. The plant of claim 5, wherein the second DNA sequence down regulates a lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl coA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH).

7. A plant part of the plant of claim 1.

8. The plant part of claim 7, further defined as a protoplast, cell, meristem, root, pistil, anther, flower, seed, embryo, stalk or petiole.

9. The plant part of claim 8, further defined as a plant seed.

10. A method for producing a commercial product, said method comprising obtaining a plant of claim 1 or a part thereof and producing a commercial product therefrom.

11. The method of claim 10, wherein the commercial product is paper, paper pulp, ethanol, biodiesel, silage, animal feed or fermentable biofuel feedstock.

12. The plant of claim 1, wherein the DNA molecule comprises at least 21 nucleotides, and wherein the DNA molecule comprises a sequence complementary to at least 19 contiguous nucleotides of SEQ ID NO:3.

13. A nucleic acid molecule comprising a nucleic acid sequence selected from the group consisting of:
   a nucleic acid comprising the sequence of SEQ ID NO: 3; or a full complement thereof (a) or (b),
      wherein the nucleic acid sequence is operably linked to a heterologous promoter sequence, and wherein expression of the nucleic acid sequence in a plant cell increases the lignin content of said plant cell.

14. The nucleic acid molecule of claim 13, wherein the heterologous promoter sequence is a developmentally-regulated, organelle-specific, inducible, tissue-specific, constitutive, cell-specific, seed specific, or germination-specific promoter.

15. A method of increasing the lignin content of a plant, said method comprising expressing a DNA molecule according to claim 13 in the plant.

16. A nucleic acid sequence comprising a unique sequence transcribed to an antisense RNA, interfering RNA, or miRNA of sufficient length that exhibits at least 96% sequence identity to SEQ ID NO: 3 or a complement thereof, wherein expression of the nucleic acid molecule in a plant cell reduces the lignin content of said plant cell compared to a plant cell not expressing the nucleic acid molecule.

17. A transgenic plant cell comprising the nucleic acid molecule of claim 16.

18. A transgenic plant or plant part comprising a nucleic acid molecule of claim 16.

19. A biofuel feedstock comprising a nucleic acid molecule of claim 16.

20. A method of increasing the level or availability of one or more fermentable carbohydrates in a biofuel crop species plant, said method comprising expressing the nucleic acid molecule of claim 1 in the plant.

21. A method of decreasing the lignin content in a plant or increasing drought tolerance, said method comprising expressing the nucleic acid molecule of claim 16 in the plant.

22. A method for increasing the digestibility of a forage crop plant, said method comprising expressing the nucleic acid molecule of claim 16 in the plant, wherein the plant is a forage plant.

* * * * *